US011061537B2

(12) United States Patent
Sahu et al.

(10) Patent No.: US 11,061,537 B2
(45) Date of Patent: Jul. 13, 2021

(54) INTERACTIVE HUMAN VISUAL AND TIMELINE ROTOR APPARATUS AND ASSOCIATED METHODS

(71) Applicant: GE Precision Healthcare LLC, Wauwatosa, WI (US)

(72) Inventors: Abhishek Sahu, Bangalore (IN); Juha Kaasinen, Kuopio (FI)

(73) Assignee: GE Precision Healthcare LLC, Wauwatosa, WI (US)

(*) Notice: Subject to any disclaimer, the term of this patent is extended or adjusted under 35 U.S.C. 154(b) by 0 days.

(21) Appl. No.: 16/661,120

(22) Filed: Oct. 23, 2019

(65) Prior Publication Data

US 2021/0124465 A1 Apr. 29, 2021

(51) Int. Cl.
| | |
|---|---|
| *G06F 3/048* | (2013.01) |
| *G06F 3/0482* | (2013.01) |
| *G16H 10/60* | (2018.01) |
| *G06F 3/0485* | (2013.01) |
| *G06F 30/20* | (2020.01) |

(52) U.S. Cl.
CPC .......... *G06F 3/0482* (2013.01); *G06F 3/0485* (2013.01); *G06F 30/20* (2020.01); *G16H 10/60* (2018.01)

(58) Field of Classification Search
None
See application file for complete search history.

(56) References Cited

U.S. PATENT DOCUMENTS

| | | | |
|---|---|---|---|
| 10,032,236 B2 | 7/2018 | Hawkins et al. | |
| 2001/0041992 A1* | 11/2001 | Lewis | G06F 19/324 705/3 |
| 2006/0277076 A1* | 12/2006 | Hasan | G16H 80/00 705/3 |
| 2008/0235057 A1 | 9/2008 | Weidenhaupt et al. | |
| 2009/0192823 A1 | 7/2009 | Hawkins et al. | |
| 2010/0050110 A1 | 2/2010 | Hughes et al. | |
| 2016/0253473 A1* | 9/2016 | Anderson | G16H 50/70 705/2 |

(Continued)

OTHER PUBLICATIONS

Imatis, "Visual Health Electronic Health Record," retrieved from www.imatis.com/imatis/ehr-overlay.htm on May 29, 2019, 6 pages.

(Continued)

*Primary Examiner* — William C Trapanese
(74) *Attorney, Agent, or Firm* — Hanley, Flight and Zimmerman, LLC

(57) ABSTRACT

Systems, apparatus, instructions, and methods for an interactive human visual and timeline rotor are disclosed. An example apparatus includes at least one processor to execute the instructions to generate at least: a digital twin of a patient, the digital twin to include models of patient health data; and a graphical user interface to provide visualization of and access to the patient health data based on an output from the digital twin. The example graphical user interface is to include: a visual representation of patient anatomy, the visual representation to include selectable indicators corresponding to the patient health data; and a rotor including categories of the patient health data, the rotor selectable via the graphical user interface to navigate a subset of the patient health data corresponding to a selected category via the visual representation of the patient.

20 Claims, 11 Drawing Sheets

(56) References Cited

U.S. PATENT DOCUMENTS

2017/0132371 A1* 5/2017 Amarasingham ..... G06F 19/328

OTHER PUBLICATIONS

Zhang et al., "AnamneVis: A Framework for the Visualization of Patient History and Medical Diagnostics Chains," Stony Brook University, retrieved on Oct. 4, 2019, 4 pages.
Jin, "Interactive Medical Record Visualization based on Symptom Location in a 2D Human Body," Thesis submitted to the Faculty of Graduate and Postdoctoral Studies in partial fulfillment of the requirements for the degree Master of Applied Science in Electrical and Computer Engineering School of Electrical Engineering and Computer Science Faculty of Engineering, University of Ottawa, Jan. 2016, 143 pages.

* cited by examiner

INTERACTIVE HUMAN VISUAL AND TIMELINE ROTOR APPARATUS AND ASSOCIATED METHODS

FIELD OF THE DISCLOSURE

This disclosure relates generally to an improved healthcare user interface and, more particularly, to an interactive human visual and timeline rotor apparatus and associated methods.

BACKGROUND

The statements in this section merely provide background information related to the disclosure and may not constitute prior art.

A clinical or healthcare environment is a crowded, demanding environment that would benefit from organization and improved ease of use of imaging systems, data storage systems, and other equipment used in the healthcare environment. A healthcare environment, such as a hospital or clinic, encompasses a large array of professionals, patients, equipment and computerized information systems. Personnel in a healthcare facility must manage a plurality of patients, systems, and tasks to provide quality service to patients. Healthcare personnel may encounter many difficulties or obstacles in their workflow.

Healthcare has become centered around electronic data and records management. Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), laboratory information systems (LIS), and electronic medical records (EMR). Information stored can include patient medication orders, medical histories, imaging data, test results, diagnosis information, management information, and/or scheduling information, for example. A wealth of information is available, but the information can be siloed in various separate systems requiring separate access, search, and retrieval. Correlations between healthcare data remain elusive due to technological limitations on the associated systems.

Different clinical departments and different clinical systems gather patient information in different ways and in different forms and often separately store that information. The information must then be retrieved and viewed from several disparate systems.

Currently, relevant patient information for a patient's entire lifetime exists in a number of formats that include paper, folders and disparate information systems from a variety of vendors and a variety of healthcare providers. Current systems cannot aggregate this information effectively. Additionally, current systems cannot display this information at one time so that healthcare providers have the ability to interpret a patient's complete medical history when assessing and diagnosing illnesses. Providers are rarely able to see the full history of a patient. More commonly, providers have only the information that they have gathered or that they have received in response to questions asked of the patient in a clinical setting. Key decisions are made with the limited knowledge available to the provider at the point at which the provider is making a decision.

Further, healthcare provider consolidations create geographically distributed hospital networks in which physical contact with systems is too costly. At the same time, referring physicians want more direct access to supporting data in reports along with better channels for collaboration. Physicians have more patients, less time, and are inundated with huge amounts of data, and they are eager for assistance. However, large datasets are necessary for computer-driven solutions, such as neural networks and other "artificial intelligence" to assist human clinicians with analysis, optimization, improvement, and/or other decision support. Such large datasets are often missing or unobtainable with current systems and restrictions.

BRIEF DESCRIPTION

Systems, apparatus, instructions, and methods for an interactive human visual and timeline rotor are disclosed.

Certain examples provide an apparatus including memory including instructions and at least one processor. The example at least one processor is to execute the instructions to generate at least: a digital twin of a patient, the digital twin to include models of patient health data; and a graphical user interface to provide visualization of and access to the patient health data based on an output from the digital twin. The example graphical user interface is to include: a visual representation of patient anatomy, the visual representation to include selectable indicators corresponding to the patient health data; and a rotor including categories of the patient health data, the rotor selectable via the graphical user interface to navigate a subset of the patient health data corresponding to a selected category via the visual representation of the patient.

Certain examples provide at least one tangible computer-readable storage medium including instructions that, when executed, cause at least one processor to at least: a digital twin of a patient, the digital twin to include models of patient health data; and a graphical user interface to provide visualization of and access to the patient health data based on an output from the digital twin. The example graphical user interface to include: a visual representation of patient anatomy, the visual representation to include selectable indicators corresponding to the patient health data; and a rotor including categories of the patient health data, the rotor selectable via the graphical user interface to navigate a subset of the patient health data corresponding to a selected category via the visual representation of the patient.

Certain examples provide a computer-implemented method to generate an interactive graphical user interface. The example method includes generating, using a digital twin of a patient, a graphical user interface including a visual representation of patient anatomy and a rotor including categories of patient health data. The example digital twin is to include models of i) patient health data and ii) patient anatomical systems. The example visual representation is to include selectable indicators corresponding to at least one of the patient health data or the patient anatomical systems. The example rotor is to be selectable via the graphical user interface to navigate a subset of the patient health data corresponding to a selected category via the visual representation of the patient. The example method includes modeling, using the digital twin when triggered by interaction with the graphical user interface, an output from at least one of the models of patient health data or the models of patient anatomical systems with respect to a criterion corresponding to at least one of an indicator or the rotor of the graphical user interface. The example method includes updating at least one of the digital twin or the graphical user interface using the output.

DETAILED DESCRIPTION OF CERTAIN EMBODIMENTS

Figure 1:
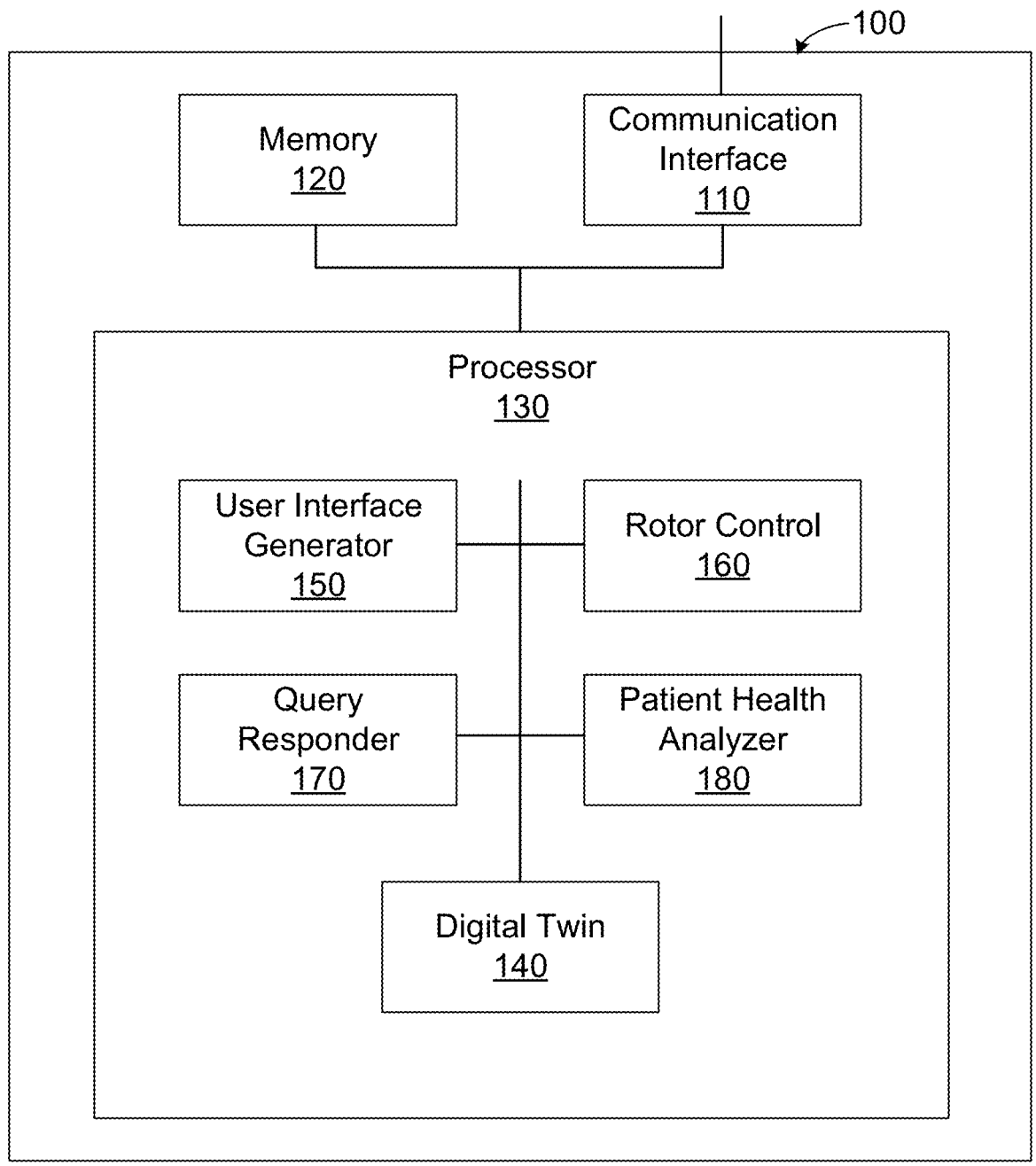
FIG. 1 is an example apparatus to generate a user interface and facilitate interaction with the user interface and associated patient health information.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an example implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object.

As used herein, the terms "system," "unit," "module," "engine," etc., may include a hardware and/or software system that operates to perform one or more functions. For example, a module, unit, or system may include a computer processor, controller, and/or other logic-based device that performs operations based on instructions stored on a tangible and non-transitory computer readable storage medium, such as a computer memory. Alternatively, a module, unit, engine, or system may include a hard-wired device that performs operations based on hard-wired logic of the device. Various modules, units, engines, and/or systems shown in the attached figures may represent the hardware that operates based on software or hardwired instructions, the software that directs hardware to perform the operations, or a combination thereof.

As used herein, singular references (e.g., "a", "an", "first", "second", etc.) do not exclude a plurality. The term "a" or "an" entity, as used herein, refers to one or more of that entity. The terms "a" (or "an"), "one or more", and "at least one" can be used interchangeably herein. Furthermore, although individually listed, a plurality of means, elements or method actions may be implemented by, e.g., a single unit or processor. Additionally, although individual features may be included in different examples or claims, these may possibly be combined, and the inclusion in different examples or claims does not imply that a combination of features is not feasible and/or advantageous.

The term "and/or" when used, for example, in a form such as A, B, and/or C refers to any combination or subset of A, B, C such as (1) A alone, (2) B alone, (3) C alone, (4) A with B, (5) A with C, (6) B with C, and (7) A with B and with C. As used herein in the context of describing structures, components, items, objects, and/or things, the phrase "at least one of A and B" is intended to refer to implementations including any of (1) at least one A, (2) at least one B, and (3) at least one A and at least one B. Similarly, as used herein in the context of describing structures, components, items, objects and/or things, the phrase "at least one of A or B" is intended to refer to implementations including any of (1) at least one A, (2) at least one B, and (3) at least one A and at least one B. As used herein in the context of describing the performance or execution of processes, instructions, actions, activities and/or steps, the phrase "at least one of A and B" is intended to refer to implementations including any of (1) at least one A, (2) at least one B, and (3) at least one A and at least one B. Similarly, as used herein in the context of describing the performance or execution of processes, instructions, actions, activities, and/or steps, the phrase "at least one of A or B" is intended to refer to implementations including any of (1) at least one A, (2) at least one B, and (3) at least one A and at least one B.

In addition, it should be understood that references to "one embodiment" or "an embodiment" of the present disclosure are not intended to be interpreted as excluding the existence of additional embodiments that also incorporate the recited features.

Certain examples provide an interactive human visual and timeline rotor for improved access to patient health history. For clinicians, reviewing overall patient health is complex and current systems lack a technological ability to provide sufficient access to overall patient health. Most existing user interfaces mandate multiple navigational actions to view patient health information. Further, if a case is complex, a clinician must do a lot of work to understand a patient's health pattern and diagnose it. Additionally, remembering and corelating three dimensions: 1) body part, 2) time, and 3) medical detail of health history becomes very complex.

Developing a pattern of health problems becomes very complex and technically challenging with existing interfaces. Further, when there are many reports and data generated with each treatment, managing and viewing the reports and data is extremely complex. To address this technological challenge, an interactive visual including all three dimensions in a single view helps a clinician to better diagnose a condition in a patient and track the progress of treatment, for example.

As such, certain examples provide a multi-dimensional view of a patient's medical history in single visual interface viewport. Interaction with an underlying system is facilitated to surface and visualize a pattern of health for the patient. Patient health is rendered progressively to identify a pattern. Certain examples provide an interactive visualization that can uncover a health pattern in more meaningful presentation for interaction such as chronic disease patterns, allergic attacks, connection between symptoms, etc., to form a pattern to diagnose and predict patient health issues.

This unique visualization of a patient's medical history shows an interactive human body representation or avatar on one side of a screen. The other side of the screen shows a time rotor with disease, symptoms and/or treatment, report and results, etc. In certain examples, each row of the rotor shows one disease, symptom and/or treatment, which is mapped to the human body visual, pointing to specific part of the human body. When a user moves the time rotor up or down, manipulation of the time rotor control advances a corresponding patient health timeline backward or forward in time and associated events, files, other data, etc.

In certain examples, a selected row of the rotor is displayed to show its included information in a more prominent way than other visible rows (e.g., larger font size, different font, highlighted, bold, more opaque, etc., compared to other displayed rows of the rotor.

In certain examples, a rotor row can be configured to show data according to a priority of information such as diagnosed disease, symptom, medication, report, etc. Additional details corresponding to a selected row can be accessed by selecting that row. Once selected, associated report(s), medical data, medication, etc., can be seen inside the selected row and/or human body anatomy representation.

In certain examples, an interactive graphical user interface providing a rotor and a human body anatomical visualization includes a plurality of modes, such as a plurality of viewer modes, each corresponding to a different type of view (e.g., cancer-related issues, neurological issues, blood pressure-related issues, etc.), an interaction mode, etc. Using a particular viewer mode, for example, a user can select one or more patients, events, indicators, etc., to combine patients, indicators, diseases, events, and/or other indicators to determine a pattern for a particular disease, condition, event, circumstance, date, etc., associated with the particular viewer mode. In certain examples, visualization and size of display elements, their proportions and inter-relationships, etc., are specified for usability and accuracy of information about patient status, patient history, predictive analytics, etc. The interactive and viewer modes incorporate patient health parameters, health history, anatomy, time/duration, and medical details in a single view via the interface, for example. This unique visualization is flexible and scalable to accommodate mobile devices, tablet displays, touch screens, augmented reality/virtual reality (AR/VR), human size displays etc. Certain examples combine the dynamic, interactive user interface with artificial intelligence (AI) to model patient information, predict patient outcome, enhance care provider decision making, etc.

Certain examples provide clinical documentation for a patient in an integrated user interface. Certain examples enable a patient's medical history to be displayed and edited by the user. A user can view a patient's information at varying levels of granularity depending upon the detail desired, for example. From a high level overall vantage point, the user may navigate to any specific item in the patient's history by using a navigational cursor, mouse click, touch screen, voice command, gaze tracking, etc. The user can drill down in a timeline, document history, workspace, etc., to view specific lab reports, physical exam notes, images, procedures, etc. In certain examples, a user can navigate a complete set of patient healthcare data via a unified interface.

A patient electronic medical record (EMR), electronic health record (EHR), and/or other record include a medical history for a patient and include data with time stamps (or times and dates at which data was collected or entered). Types of data can include test name, test result, imaging acquisition, medical visit (e.g., hospital, office, clinic, etc.), medical problem, caregiver encounter, medical procedure, symptom, biological analysis, finding, medication, acquisition, etc. These types/categories of data can each be represented by a symbol on a common and/or individual timeline for each event of the data occurrence, for example.

Medical data can be obtained from imaging devices, sensors, laboratory tests, and/or other data sources. Alone or in combination, medical data can assist in diagnosing a patient, treating a patient, forming a profile for a patient population, influencing a clinical protocol, etc. However, to be useful, medical data must be organized properly for analysis and correlation beyond a human's ability to track and reason. Computers and associated software and data constructs can be implemented to transform disparate medical data into actionable results.

For example, imaging devices (e.g., gamma camera, positron emission tomography (PET) scanner, computed tomography (CT) scanner, X-Ray machine, magnetic resonance (MR) imaging machine, ultrasound scanner, etc.) generate two-dimensional (2D) and/or three-dimensional (3D) medical images (e.g., native Digital Imaging and Communications in Medicine (DICOM) images) representative of the parts of the body (e.g., organs, tissues, etc.) to diagnose and/or treat diseases. Other devices such as electrocardiogram (ECG) systems, echoencephalograph (EEG), pulse oximetry (SpO2) sensors, blood pressure measuring cuffs, etc., provide one-dimensional waveform and/or time series data regarding a patient.

In certain examples, patient data can be presented visually via a timeline including one or more symbols representing each patient encounter. A patient encounter can include any test, visit, or other encounter with any physician, nurse, radiologist, image technician or other caregiver, for example. With many patient encounters, the timeline can become too cluttered rendering it difficult to view individual data items and visualize associations between data. Data can be associated in a number of ways, such as by patient encounter (e.g., office/hospital visit/stay), time/date range, problem (e.g., diabetes, heart disease, broken bone, etc.), procedure (e.g., surgery, series of lab tests, etc.), collecting/entering hospital/clinic/caregiver, etc.

In certain examples, a patient medical record includes aggregated information from a plurality of information systems under a common patient context. Information systems may include a radiology information system (RIS), a picture archiving and communication system (PACS), Computer Physician Order Entry (CPOE), an electronic medical record (EMR), Clinical Information System (CIS), Cardiovascular Information System (CVIS), Library Information System (LIS), and/or other healthcare information system (HIS), for example. An integrated user interface facilitating access to the patient record can include a context manager, such as a clinical context object workgroup (CCOW) context manager and/or other rules-based context manager. Components can communicate via wired and/or wireless connections on one or more processing units, such as computers, medical systems, storage devices, custom processors, and/or other processing units. Components can be implemented separately and/or integrated in various forms in hardware, software and/or firmware, for example.

Information for a particular patient can be extracted and/or linked from one or more information systems for presentation to a user via a patient timeline and associated information viewer, for example. In certain examples, information retrieval, display and/or processing settings, for example, can be customized according to a particular user or type of user. Retrieval, aggregation, display and/or processing of information can be based on rules, preferences, and/or other settings, for example. Rules, preferences, settings, etc. can be generated automatically based on preset parameters and/or observed data, for example. Rules, preferences, settings, etc., can be created by a system administrator or other user, for example. Rules, preferences, settings, etc., also can be manually and/or automatically adapted based on user and/or automated system experiences, for example.

In certain examples, a patient record provides identification information, allergy and/or ailment information, history information, orders, medications, progress notes, flow-sheets, labs, images, monitors, summary, administrative information, and/or other information, for example. The patient record can include a list of tasks for a healthcare practitioner and/or the patient, for example. The patient record can also identify a care provider and/or a location of the patient, for example.

In certain examples, an indication can be given of, for example, normal results, abnormal results, and/or critical results. For example, the indication can be graphical, such as an icon. The user can select the indicator to obtain more information. For example, the user can click on an icon to see details as to why a result was abnormal. In certain examples, the user may be able to view only certain types of results. For example, the user may only be eligible to and/or may only select to view critical results.

In certain examples, filters and/or rules can be provided for application to one or more views and/or categories. Ranges, such as values or dates, can be specified for data. Default views, categories, filters, rules, and/or ranges can be provided. In certain examples, default values can be modified by a user and/or based on operating conditions. In certain examples, new views, categories, filters, rules, ranges, etc., can be created by a user.

For example, a filter can be used to filter medical results data presented to a user according to one or more variables or parameters. For example, when a filter is selected by a user, a modification routine applies the filter to the results displayed to the user in the current view by removing from display all medical results that do not fall within the filter. For example, a variable/parameter can include one or more of a type (or item) and/or range of laboratory test results, vital sign measurements, fluids administered to a patient, and/or fluids measured from a patient. A variable/parameter can include text from notes, laboratory reports, examination reports, one or more captions to a laboratory test result, vital sign measurement, and/or fluids administered to/measured from a patient, an order for a laboratory test, treatment and/or prescription, and/or a name, for example. By specifying one or more limits on one or more variables and/or one or more restricting parameters, a user can create one or more filters to be applied to results presented in a results window.

In certain examples, an integrated user interface viewer is in communication with one or more applications and/or information systems. The integrated user interface interacts with individual application(s) and/or system(s) and masks or hides the individual application(s) and/or system(s) from a user. That is, the user sees and interacts with the integrated user interface viewer rather than with interfaces for individual connected application(s) and/or system(s), for example. A user can be authenticated via the integrated user interface, and that authentication can propagate throughout the connected application(s) and/or system(s), for example.

In certain examples, a digital model or "twin" can be created of a patient to represent and/or be paired with the patient's medical record/history information. For example, a digital representation, digital model, digital "twin", or digital "shadow" is a digital informational construct about a physical system. That is, digital information can be implemented as a "twin" of a physical device/system/person and information associated with and/or embedded within the physical device/system/person. The digital twin is linked with the physical object through the lifecycle of the physical object. In certain examples, the digital twin includes a physical patient in real space, a digital twin of that physical patient that exists in a virtual space, and information linking the physical patient with his/her digital twin. The digital twin exists in a virtual space corresponding to a real space and includes a link for data flow from real space to virtual space as well as a link for information flow from virtual space to real space and virtual sub-spaces.

Machine learning techniques, whether deep learning networks or other experiential/observational learning system, can be used to characterize and otherwise interpret, extrapolate, conclude, and/or complete acquired medical data from a patient, for example. Deep learning is a subset of machine learning that uses a set of algorithms to model high-level abstractions in data using a deep graph with multiple processing layers including linear and non-linear transformations. While many machine learning systems are seeded with initial features and/or network weights to be modified through learning and updating of the machine learning network, a deep learning network trains itself to identify "good" features for analysis. Using a multilayered architecture, machines employing deep learning techniques can process raw data better than machines using conventional machine learning techniques. Examining data for groups of highly correlated values or distinctive themes is facilitated using different layers of evaluation or abstraction.

Deep learning is a class of machine learning techniques employing representation learning methods that allows a machine to be given raw data and determine the representations needed for data classification. Deep learning ascertains structure in data sets using backpropagation algorithms which are used to alter internal parameters (e.g., node weights) of the deep learning machine. Deep learning machines can utilize a variety of multilayer architectures and algorithms. While machine learning, for example, involves an identification of features to be used in training the network, deep learning processes raw data to identify features of interest without the external identification.

Deep learning in a neural network environment includes numerous interconnected nodes referred to as neurons. Input neurons, activated from an outside source, activate other neurons based on connections to those other neurons which are governed by the machine parameters. A neural network behaves in a certain manner based on its own parameters. Learning refines the machine parameters, and, by extension, the connections between neurons in the network, such that the neural network behaves in a desired manner.

A variety of artificial intelligence networks can be deployed to process input data. For example, deep learning that utilizes a convolutional neural network (CNN) segments data using convolutional filters to locate and identify learned, observable features in the data. Each filter or layer of the CNN architecture transforms the input data to increase the selectivity and invariance of the data. This abstraction of the data allows the machine to focus on the features in the data it is attempting to classify and ignore irrelevant background information.

Deep learning operates on the understanding that many datasets include high level features which include low level features. While examining an image, for example, rather than looking for an object, it is more efficient to look for edges which form motifs which form parts, which form the object being sought. These hierarchies of features can be found in many different forms of data such as speech and text, etc.

Learned observable features include objects and quantifiable regularities learned by the machine during supervised learning. A machine provided with a large set of well classified data is better equipped to distinguish and extract the features pertinent to successful classification of new data.

A deep learning machine that utilizes transfer learning may properly connect data features to certain classifications affirmed by a human expert. Conversely, the same machine can, when informed of an incorrect classification by a human expert, update the parameters for classification. Settings and/or other configuration information, for example, can be guided by learned use of settings and/or other configuration information, and, as a system is used more (e.g., repeatedly and/or by multiple users), a number of variations and/or other possibilities for settings and/or other configuration information can be reduced for a given situation.

An example deep learning neural network can be trained on a set of expert classified data, for example. This set of data builds the first parameters for the neural network, and this would be the stage of supervised learning. During the stage of supervised learning, the neural network can be tested whether the desired behavior has been achieved.

Once a desired neural network behavior has been achieved (e.g., a machine has been trained to operate according to a specified threshold, etc.), the machine can be deployed for use (e.g., testing the machine with "real" data, etc.). During operation, neural network classifications can be confirmed or denied (e.g., by an expert user, expert system, reference database, etc.) to continue to improve neural network behavior. The example neural network is then in a state of transfer learning, as parameters for classification that determine neural network behavior are updated based on ongoing interactions. In certain examples, the neural network can provide direct feedback to another process. In certain examples, the neural network outputs data that is buffered (e.g., via the cloud, etc.) and validated before it is provided to another process.

Deep learning machines can utilize transfer learning when interacting with physicians to counteract the small dataset available in the supervised training. These deep learning machines can improve their computer aided diagnosis over time through training and transfer learning. However, a larger dataset results in a more accurate, more robust deployed deep neural network model that can be applied to transform disparate medical data into actionable results (e.g., system configuration/settings, computer-aided diagnosis results, image enhancement, etc.).

Certain examples can leverage one or more deep learning constructs to form a digital twin, to predict an outcome with respect to all or part of a digital twin, to correlate a reason for exam, a query, new information, etc., with a digital twin and/or other modeling of patient health, etc. As such, a predicted outcome, a computer-assisted diagnosis, etc., can be driven by a digital twin, taken alone and/or in conjunction with one or more deep learning and/or other machine learning models, constructs, devices, etc.

FIG. 1 illustrates an example apparatus 100 to generate a user interface and facilitate interaction with the user interface and associated patient health information, modeling, predictive analytics, scheduling, registration, evaluation, etc. The example user interface generation and control apparatus 100 includes a communication interface 110, memory 120, and a processor 130. The example memory 120 can include instructions to, when executed by the processor 130, generate a digital twin 140. The example processor 130 also provides a user interface generator 150 to generate and facilitate interaction with a graphical user interface, such as via the example communication interface 110. The example processor 130 also includes a rotor control 160, a query responder 170, and a patient health analyzer 180.

The example processor 130 can receive a request, query, and/or other trigger via the communication interface 110 and generate and/or update the graphical user interface using the user interface generator 150 and the query responder 170, for example. In certain examples, the user interface generator 150 generates the graphical user interface including a visual representation of a patient's anatomy and associated health history (e.g., events, images, operations, vitals, other data, etc.) along with a rotor or wheel associated with the patient's medical data. The rotor is generated and controlled using the rotor control 160. The rotor is tied to the visual representation of patient anatomy and displays the patient's health data according to category/type, timeline, event, etc. For example, the query responder 170 processes a user, application, and/or system query, request, command, etc., (e.g., received via the communication interface 110, etc.) and triggers generation and/or update of content to the interface generator 150, rotor control 160, patient health analyzer 180, digital twin 140, etc. In certain examples, the query responder 170 processes a change in mode, which triggers a change in information displayed for selection via the rotor. In such examples, the rotor control 160 updates information displayed on the rotor, option(s) for manipulation and/or other control of the rotor, etc., based on the selected mode.

In certain examples, the rotor allows a user to transition through the patient's entire life cycle according to the health/medical data stored and/or otherwise accessible by the processor 130 for the patient. For example, the rotor can be used to scroll through a list or set of events and/or other data points related to the patient's health/medical history. Manipulating the rotor triggers a change in the visual representation of the patient anatomy and corresponding health data to be displayed via the graphical user interface. As such, the rotor control 160 can communicate with the user interface generator 150 to update the graphical user interface as rotor interaction occurs. For example, as the rotor moves, indicators displayed on the virtual representation of the anatomy change in correspondence with the visible and/or otherwise selected line of the rotor. As such, a visualization and correlation are provided to determine how the patient's health changes over time, how a problem moves from one place to another in the patient's anatomy over time, etc. The evolution of the patient's body and associated health can be determined, modeled, and conveyed over time. The digital twin of the patient, paired with the visual representation, rotor, and associated health data, models user health, behavior, progression, actual and/or predicted reaction to treatment, etc. As such, the rotor control 160 and user interface generator 150 can also operate to update and/or otherwise manipulate (e.g., execute an AI model, etc.) the digital twin 140, for example.

In certain examples, the rotor provides a viewer mode selector to select a particular viewer mode (e.g., a cancer-related viewer mode, a neurological-related viewer mode, a circulatory-related viewer mode, an injury-related viewer mode, a cardiac-related viewer model, a musculoskeletal-related viewer mode, etc.), which triggers filtering and display of medical data, events, exams, indicators, etc., associated with that particular viewer mode. Such selection triggers a change in the virtual representation of the patient's anatomy, rotor data, medical data displayed, etc. Thus, based on disease type, system, etc., a mode selector can enable an AI model to filter available health data to display, process, enable interaction with, etc., only a subset of the data relating to the condition(s) associated with the mode/filter, for example.

The digital twin 140 can be updated based on a query, rotor selection, mode, patient health information update, etc. In certain examples, an AI model associated with the digital twin 140 can process a query input and provide an output prediction and/or other result, etc. For example, a query of patient medications can be processed by an AI model of the digital twin 140 to identify a reaction (or likelihood of reaction) among the current and/or proposed medications in the query with respect to the particular patient modeled by the digital twin 140. Thus, the patient's history, allergies, sensitivities, and/or mediations, etc., can be modeled in combination with one or more proposed medications to determine potential for adverse reaction, for example.

In certain examples, selection of a rotor segment provides feedback to the rotor control 160. The rotor control 160 transmits the rotor segment selection (e.g., a particular event, time, exam, category, type, etc.) to the query responder 170. The query responder 170 can access information from the digital twin 140 and/or leverage the patient health analyzer 180 to answer a query posed by the rotor selection such as retrieval of certain health information, correlation of an event with patient health data, combination of disparate health data with respect to a certain date or time period, condition, disease, location, etc.

The patient health analyzer 180 can also process a selection from the rotor control 160 and/or information from the communication interface 110, query responder 170, interface generator 150, digital twin 140, etc., and determine a patient's health status, determine/predict an effect on patient health, correlate the patient's health with another patient's health, condition, time period, and/or location, for example.

In certain examples, an output of the patient health analyzer 180 and/or the digital twin 140 can be formulated by the query responder 170 into an output to be displayed via the interface by the user interface generator 150. The query responder 170 can also provide a processed output to another application, system, device, user, etc., via the communication interface 110, for example. As such, the digital twin 140, patient health analyzer 180, etc., can react to input data, input query, change in mode and/or other rotor state, indicator selection, etc., to generate an output to drive another process, application, system, device, etc.

Figure 2:
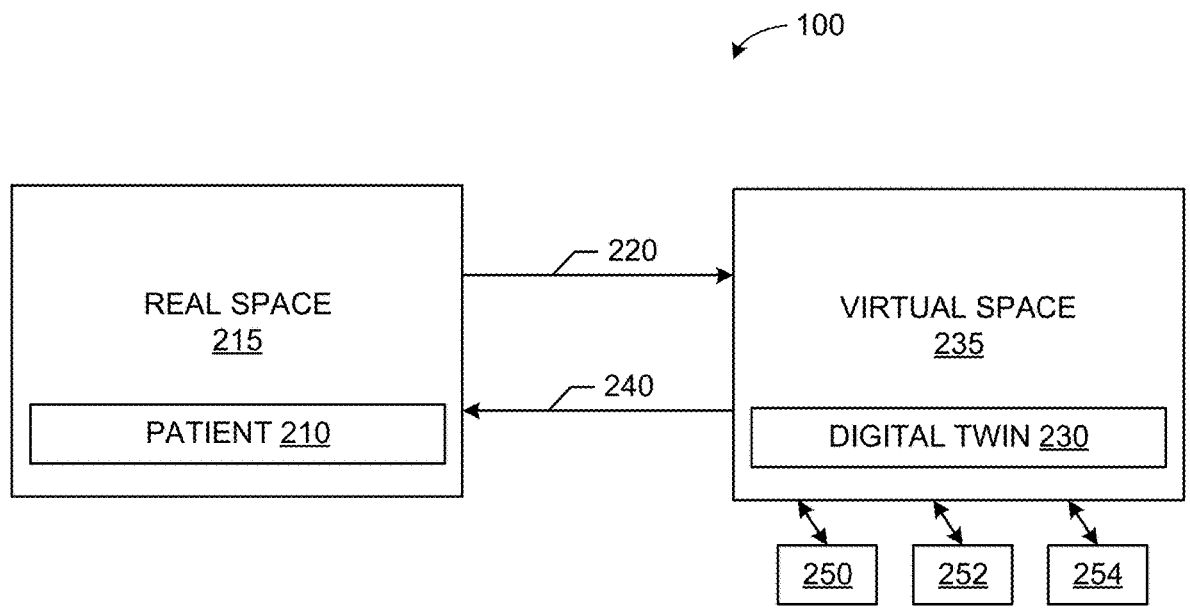
FIG. 2 illustrates an example relationship between an actual patient and a digital twin of that patient.

FIG. 2 illustrates an example relationship between an actual patient and a digital twin of that patient, which can drive display of patient health data, correlation of patient health data, computer-assisted diagnosis of condition and/or treatment, etc., via the example system 100 and its graphical user interface, for example. FIG. 2 illustrates a patient 210 in a real space 215 providing data 220 to a digital twin 230 in a virtual space 235. The digital twin 230 and/or its virtual space 235 provide information 240 back to the real space 215. The digital twin 230 and/or virtual space 235 can also provide information to one or more virtual sub-spaces 250, 252, 254. As shown in the example of FIG. 2, the virtual space 235 can include and/or be associated with one or more virtual sub-spaces 250, 252, 254, which can be used to model one or more parts of the digital twin 230 and/or digital "sub-twins" modeling subsystems/subparts of the overall digital twin 230.

In certain examples, one or more health information systems, users, and/or sensors connected to the patient 210 can collect data and relay the collected data 220 to the digital twin 230 (e.g., via self-reporting, using a clinical or other health information system such as a picture archiving and communication system (PACS), radiology information system (RIS), electronic medical record system (EMR), laboratory information system (LIS), cardiovascular information system (CVIS), hospital information system (HIS), and/or combination thereof, etc.). Interaction between the digital twin 230 and the patient 210 can help improve diagnosis, treatment, health maintenance, etc., for the patient 210, for example. An accurate digital description 230 of the patient 210 benefiting from a real-time or substantially real-time (e.g., accounting from data transmission, processing, and/or storage delay) allows the system 200 to predict "failures" in the form of disease, body function, and/or other malady, condition, etc.

In certain examples, obtained images overlaid with sensor data, lab results, etc., can be used in augmented reality (AR) applications when a healthcare practitioner is examining, treating, and/or otherwise caring for the patent 210. Using AR, the digital twin 230 follows the patient's response to the interaction with the healthcare practitioner, for example. The response can be conveyed in the user interface via the visual representation of the patient and associated rotor, driven by the digital twin 230, for example.

Thus, rather than a generic model, the digital twin 230 is a collection of actual physics-based, anatomically-based, and/or biologically-based models reflecting the patient 210 and his or her associated norms, conditions, etc. In certain examples, three-dimensional (3D) modeling of the patient 210 creates the digital twin 230 for the patient 210. The digital twin 230 can be used to view a status of the patient 210 based on input data 220 dynamically provided from a source (e.g., from the patient 210, practitioner, health information system, sensor, etc.).

In certain examples, the digital twin 230 of the patient 210 can be used for monitoring, diagnostics, and prognostics for the patient 210. Using sensor data in combination with historical information, current and/or potential future conditions of the patient 210 can be identified, predicted, monitored, etc., using the digital twin 230. Causation, escalation, improvement, etc., can be monitored via the digital twin 230. Using the digital twin 230, the patient's 210 physical behaviors can be simulated and visualized for diagnosis, treatment, monitoring, maintenance, etc.

In contrast to computers, humans do not process information in a sequential, step-by-step process. Instead, people try to conceptualize a problem and understand its context. While a person can review data in reports, tables, etc., the person is most effective when visually reviewing a problem and trying to find its solution. Typically, however, when a person visually processes information, records the information in alphanumeric form, and then tries to re-conceptualize the information visually, information is lost and the problem-solving process is made much less efficient over time.

Using the digital twin 230, however, allows a person and/or system to view and evaluate a visualization of a situation (e.g., a patient 210 and associated patient problem, etc.) without translating to data and back. With the digital twin 230 in common perspective with the actual patient 210, physical and virtual information can be viewed together, dynamically and in real time (or substantially real time accounting for data processing, transmission, and/or storage delay). Rather than reading a report, a healthcare practitioner can view and simulate with the digital twin 230 to evaluate a condition, progression, possible treatment, etc., for the patient 210. In certain examples, features, conditions, trends, indicators, traits, etc., can be tagged and/or otherwise labeled in the digital twin 230 to allow the practitioner to quickly and easily view designated parameters, values, trends, alerts, etc., such as via the visual representation of the patient via the graphical user interface. In certain examples, the rotor linked to the visual representation and associated digital twin 230 is modified by the digital twin 230 to include certain options for selection, highlight certain options, etc.

The digital twin 230 can also be used for comparison (e.g., to the patient 210, to a "normal", standard, or reference patient, set of clinical criteria/symptoms, etc.). In certain examples, the digital twin 230 of the patient 210 can be used to measure and visualize an ideal or "gold standard" value state for that patient, a margin for error or standard deviation around that value (e.g., positive and/or negative deviation from the gold standard value, etc.), an actual value, a trend of actual values, etc. A difference between the actual value or trend of actual values and the gold standard (e.g., that falls outside the acceptable deviation) can be visualized as an alphanumeric value, a color indication, a pattern, etc.

Further, the digital twin 230 of the patient 210 can facilitate collaboration among friends, family, care providers, etc., for the patient 210. Using the digital twin 230, conceptualization of the patient 210 and his/her health can be shared (e.g., according to a care plan, etc.) among multiple people including care providers, family, friends, etc. People do not need to be in the same location as the patient 210, with each other, etc., and can still view, interact with, and draw conclusions from the same digital twin 230, for example.

Thus, the digital twin 230 can be defined as a set of virtual information constructs that describes (e.g., fully describes) the patient 210 from a micro level (e.g., heart, lungs, foot, anterior cruciate ligament (ACL), stroke history, etc.) to a macro level (e.g., whole anatomy, holistic view, skeletal system, nervous system, vascular system, etc.). In certain examples, the digital twin 230 can be a reference digital twin (e.g., a digital twin prototype, etc.) and/or a digital twin instance. The reference digital twin represents a prototypical or "gold standard" model of the patient 210 or of a particular type/category of patient 210, while one or more reference digital twins represent particular patients 210. Thus, the digital twin 230 of a child patient 210 may be implemented as a child reference digital twin organized according to certain standard or "typical" child characteristics, with a particular digital twin instance representing the particular child patient 210. In certain examples, multiple digital twin instances can be aggregated into a digital twin aggregate (e.g., to represent an accumulation or combination of multiple child patients sharing a common reference digital twin, etc.). The digital twin aggregate can be used to identify differences, similarities, trends, etc., between children represented by the child digital twin instances, for example.

In certain examples, the virtual space 235 in which the digital twin 230 (and/or multiple digital twin instances, etc.) operates is referred to as a digital twin environment. The digital twin environment 235 provides an integrated, multi-domain physics- and/or biologics-based application space in which to operate the digital twin 230. The digital twin 230 can be analyzed in the digital twin environment 235 to predict future behavior, condition, progression, etc., of the patient 210, for example. The digital twin 230 can also be interrogated or queried in the digital twin environment 235 to retrieve and/or analyze current information 240, past history, etc.

In certain examples, the digital twin environment 235 can be divided into multiple virtual spaces 250-254. Each virtual space 250-254 can model a different digital twin instance and/or component of the digital twin 230 and/or each virtual space 250-254 can be used to perform a different analysis, simulation, etc., of the same digital twin 230. Using the multiple virtual spaces 250-254, the digital twin 230 can be tested inexpensively and efficiently in a plurality of ways while preserving patient 210 safety. A healthcare provider can then understand how the patient 210 may react to a variety of treatments in a variety of scenarios, for example.

Figure 3:
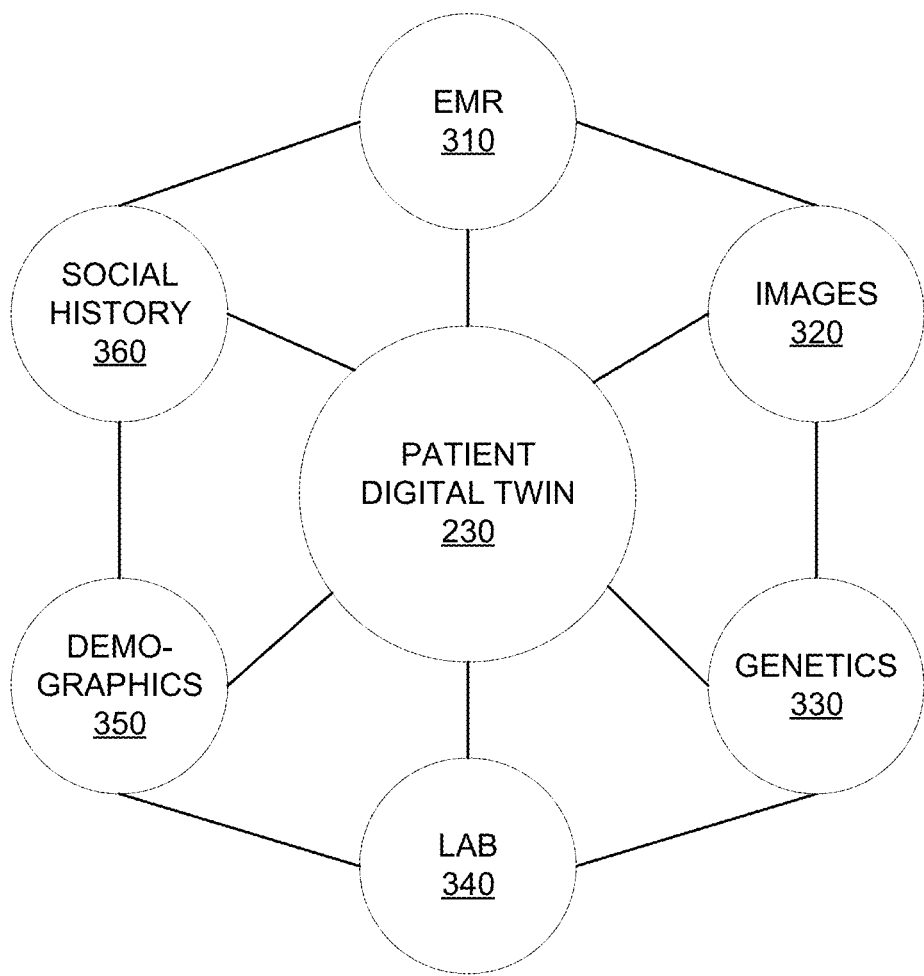
FIGS. 3-4 illustrate example implementations of the digital twin.

FIG. 3 illustrates an example implementation of the patient digital twin 230. The patient digital twin 230 includes electronic medical record (EMR) 310 information, images 320, genetic data 330, laboratory results 340, demographic information 350, social history 360, etc. As shown in the example of FIG. 3, the patient digital twin 230 is fed from a plurality of data sources 310-360 to model the patient 210. Using the plurality of sources of patient 210 information, the patient digital twin 230 can be configured, trained, populated, etc., with patient medical data, exam records, patient and family history, lab test results, prescription information, friend and social network information, image data, genomics, clinical notes, sensor data, location data, etc.

When a user (e.g., the patient 210, patient family member (e.g., parent, spouse, sibling, child, etc.), healthcare practitioner (e.g., doctor, nurse, technician, administrator, etc.), other provider, payer, etc.) and/or program, device, system, etc., inputs data in a system such as a picture archiving and communication system (PACS), radiology information system (RIS), electronic medical record system (EMR), laboratory information system (LIS), cardiovascular information system (CVIS), hospital information system (HIS), population health management system (PHM) etc., that information is reflected in the digital twin 230. Thus, the patient digital twin 230 can serve as an overall model or avatar of the patient 210 and can also model particular aspects of the patient 210 corresponding to particular data source(s) 310-360. Data can be added to and/or otherwise used to update the digital twin 230 via manual data entry and/or wired/wireless (e.g., WiFi™, Bluetooth™, Near Field Communication (NFC), radio frequency, etc.) data communication, etc., from a respective system/data source, for example. Data input to the digital twin 230 is processed by the processor 130 to normalize the information and provide governance and/or management rules, criteria, etc., to the information. In certain examples, in addition to building the digital twin 230, some or all information can also be aggregated for population-based health analytics, management, etc.

Figure 4:
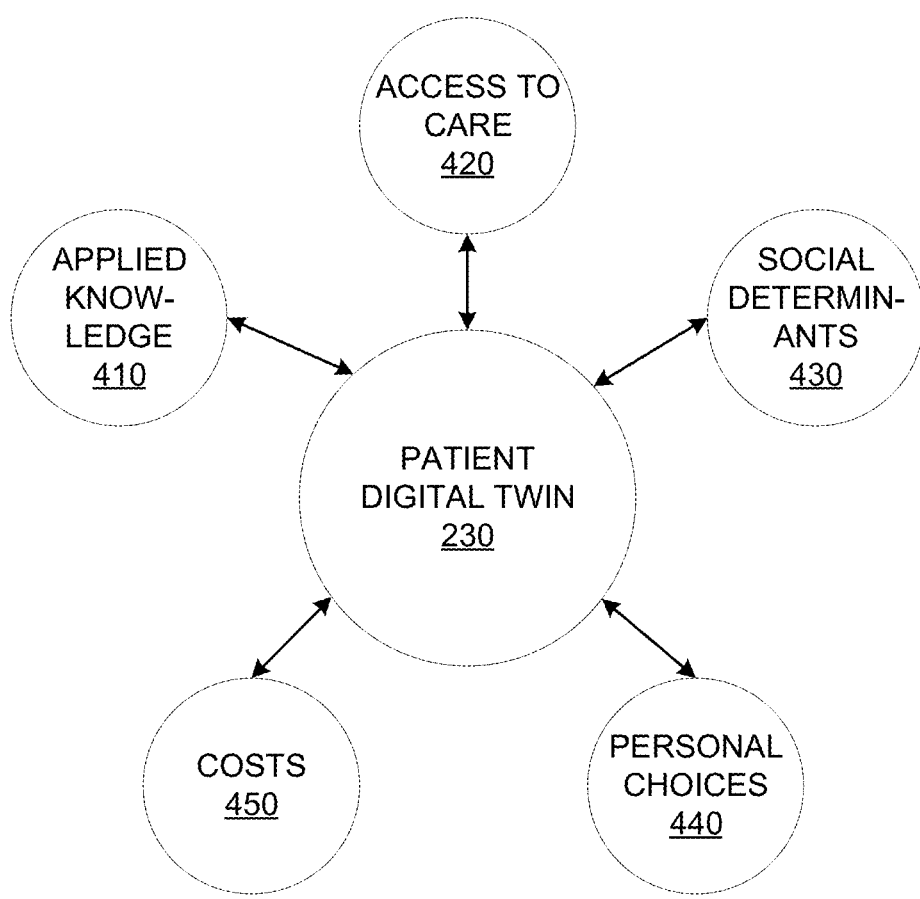

FIG. 4 illustrates an example relationship between the patient digital twin 230 and advanced coordinated technologies to achieve patient outcomes. The patient digital twin 230 can be used to apply patient-related heterogenous data with artificial intelligence (e.g., machine learning, deep learning, etc.) and digitized medical knowledge to enable health outcomes. As shown in the example of FIG. 4, the patient digital twin 230 can be used to drive applied knowledge 410, access to care 420, social determinants 430, personal choices 440, costs 450, etc.

For example, digital medical knowledge 410 includes clinical evidence, other literature, algorithms, processing engines, other governance and management, etc. Information regarding access to care 420 includes clinic access, hospital access, home access, telemedicine access, etc. Information regarding access to care can include and/or be generated by clinicians and/or other healthcare practitioners associated with the patient 210. In certain examples, a plurality of systems such as workflow, communications, collaboration, etc., can impact access to care 420 by the patient 210. Such systems can be modeled at the clinical, hospital, home, and telemedicine level via the patient digital twin 230. Such systems can provide information to the digital twin 230, for example.

Information regarding behavioral choices 440 includes diet, exercise, alcohol, tobacco, drugs, sexual behavior, extreme sports, hygiene, etc. Behavioral information can be provided by the patient 210, clinicians, other healthcare practitioners, coaches, social workers, family, friends, etc. Additionally, behavioral information can be provided by medical devices, monitoring devices, biometric sensors, locational sensors, communication systems, collaboration systems, etc. Behavioral choices 440 observed in and/or documented with respect to the patient 210 can be reflected in the patient's digital twin 230, and rules, consequences, and/or other outcomes of certain behaviors can be modeled via the digital twin 230, for example.

Information regarding environmental factors 430 can include home, air, water, pets, chemicals, family, etc. Thus, one or more social/environmental factors 430 can be modeled for the patient 210 via the patient's digital twin 230. In certain examples, community resources, medical devices, monitoring devices, biometric sensors, locational sensors, communication systems, collaboration systems, etc., can be used to measure and/or otherwise capture social/environmental information 430 to be modeled via the patient digital twin 230, for example. Social/environmental factors can influence patient 210 behavior, health, recovery, adherence to protocol, etc., and such factors can be modeled by the digital twin 230, for example.

Information regarding costs 450 can include people, diagnosis, therapy, bricks and mortar, technology, legal and insurance, materials, etc. Thus, one or more costs 450 can be modeled for the patient 210 via the patient's digital twin 230. Estimated cost 450 associated with a particular recommendation for action, treatment, prevention, etc., can be evaluated based at least in part on cost 450 via the patient digital twin 230. An estimate of current cost 450 for the patient 210 can be calculated and tracked via the digital twin 230, for example. Costs 450 such as people, diagnosis, therapy, bricks and mortar, technology, legal and insurance, materials, etc., can be captured, output, and/or evaluated using one or more data sources, people, systems, etc. For example, data sources such as settings, supply chain information, people, operations, etc., can provide cost 450 information. People in a variety of roles and/or settings can provide cost 450 information, for example. Systems such as clinical systems, financial systems, operational systems, analytical systems, etc., can provide and/or leverage cost 450 information, for example. Thus, expenses for people (e.g., healthcare practitioners, care givers, family, etc.), diagnosis (e.g., laboratory tests, images, etc.), therapy (e.g., physical therapy, mental therapy, occupational therapy, etc.), bricks and mortar (e.g., rent, lodging, transportation, etc.), technology (e.g., sensors, medical devices, computer, etc.), legal and insurance (e.g., attorney fees, health insurance, etc.), materials (e.g., test strips, kits, first aid supplies, ambulatory aids, etc.), etc., can be modeled via the digital twin 230 and/or can serve as input to refine/improve the model of the digital twin 230 for the patient (e.g., including via simulation and/or other "what if" analysis, etc.).

As modeled with the digital twin 230 in the example of FIGS. 2-4, a health outcome can be determined as follows:

$$\frac{[\text{Patient Digital Twin}] * [\text{Digital Medical Knowledge}] * [\text{Access to Care}]}{[\text{Behavioral Choices}] * [\text{Social/Physical Environment}] * [\text{Costs}]} = \text{Health Outcomes.} \quad (\text{Eq. 1})$$

In certain examples, a solutions architecture of collaboration connecting workflows driven by analytics running on a cloud and/or on-premise platform can facilitate determination of health outcomes using the patient digital twin 230 and Equation 1.

In certain examples, as set forth in Equation 1, a combination of the patient digital twin 230 modeled with digital medical knowledge 410 and access to care 420, bounded by behavioral choices 440, social/physical environment 430 and cost 450, provides a prediction, estimation, and/or other determination of health outcome for the patient 210. Such a combination represents a technological improvement in computer-aided diagnosis and treatment of patients, as the patient digital twin 230 represents a new and improved data structure and automated, electronic correlation with digital medical knowledge 410 and access to care 420, bounded by behavioral choices 440, social/physical environment 430 and cost 450, enables modeling, simulation, and identification of potential issues and possible solutions not feasible when done manually by a clinician or by prior computing systems, which were unable to model and simulate as the patient digital twin 230 disclosed and described herein. As such, the patient digital twin 230 can be used to help drive a continuous loop of patient care in conjunction with the processor 130 and associated graphical user interface, for example.

Figure 5:
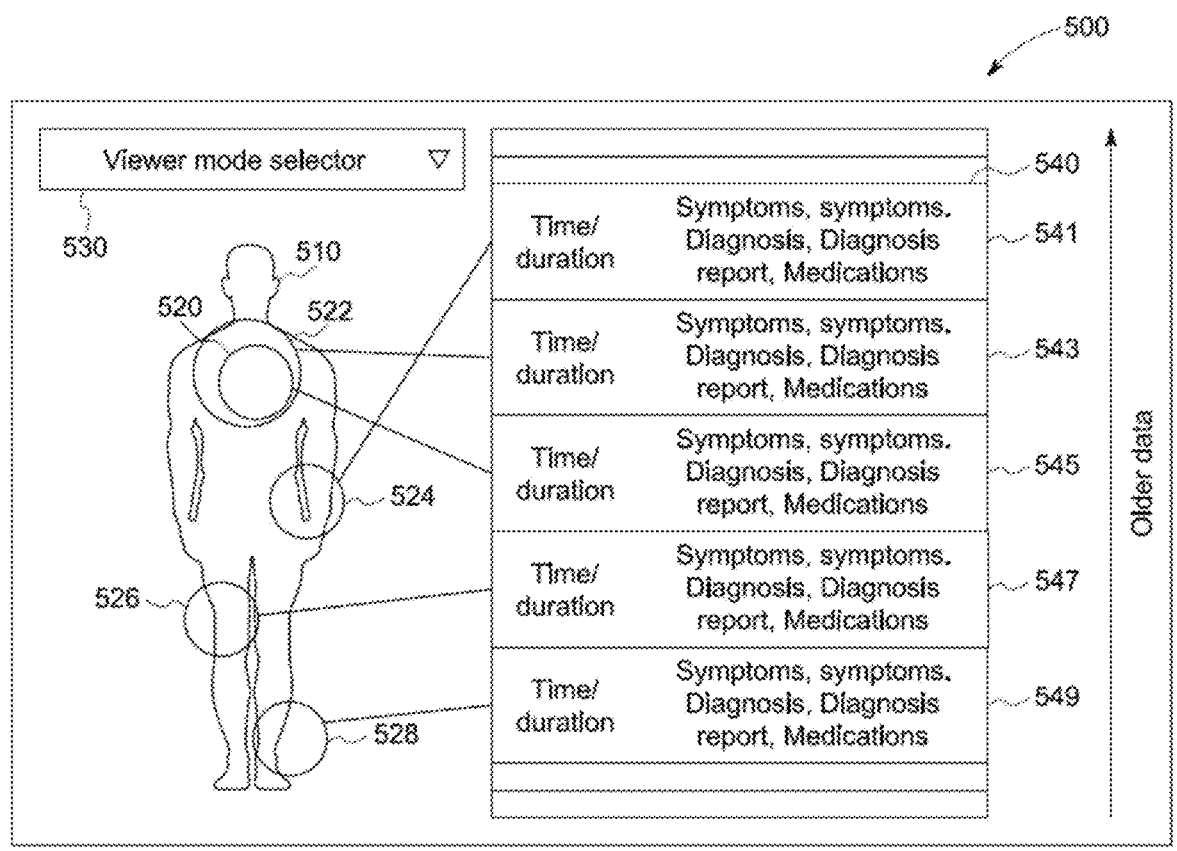
FIGS. 5-7 show example graphical user interfaces generated by the user interface generator of the example of FIG. 1.

FIG. 5 shows an example graphical user interface 500 generated by the user interface generator 150. The example interface 500 includes a visual representation (also referred to as a graphical representation) 510 of the patient's anatomy including one or more indicators 520-528 corresponding to patient health data, events, reminders, alerts, etc. The visual representation 510 can be operationally connected to a viewer mode selector 530 such that a selection of a mode via the viewer more selector 530 triggers a change in the visual representation 510 (e.g., a change in indicators 520-528 displayed with respect to (e.g., on, in, around, etc.) the visual representation 510 based on the selected mode, etc.).

For example, the viewer mode selector 530 can enable selection among a plurality of modes such as a cancer-related viewer mode, a neurological-related viewer mode, a circulatory-related viewer mode, an injury-related viewer mode, a cardiac-related viewer model, a musculoskeletal-related viewer mode, etc. Selection of a mode via the selector 530 triggers filtering and display of medical data, events, exams, indicators, etc., associated with that particular viewer mode. Such selection triggers a change in the virtual representation of the patient's anatomy, rotor data, medical data displayed, etc. Thus, based on disease type, system, etc., the mode selector 530 can enable an AI model to filter available health data to display, process, enable interaction with, etc., only a subset of the data relating to the condition(s) associated with the mode/filter via the visual representation 510 and its indicators 520-528, for example.

A rotor 540 provides patient health-related information according to patient, viewer mode, date, category, etc. Each entry or record 541-549 on the rotor 540 displays different indicators 520-528 and/or associated information with respect to the visual representation 510 of the patient via the user interface 500. For example, each segment 541-549 of the rotor 540 provides one or more symptoms, diagnosis, report, medication, etc., at a particular time and/or duration. In certain examples, a selected rotor 540 segment 541-549 corresponds to a plurality of indicators 520-528 displayed with respect to the visual representation 510. In other examples, each rotor 540 segment 541-549 corresponds to a particular indicator 520-528 of the visual representation 510. In certain examples, one indicator 520 can represent a subset, a portion, a particular instance, etc., of a larger indicator 522 such that multiple indicators 520-522 cover a same or overlapping portion of the patient anatomy reflected in the visual representation 510.

In certain examples, each indicator 520-528 corresponds to a report, event, waveform, image, lab result, and/or other source document, and selection of an indicator 520-528 triggers display of the source document via the interface 500. In certain examples, dragging the rotor 540 up exposes more recent medical history and association with indicators 520-528 of the visual representation 510, and pulling the rotor 540 down reveals older medical history and association with the visual representation 510 and its indicators 520-528.

Figure 6:
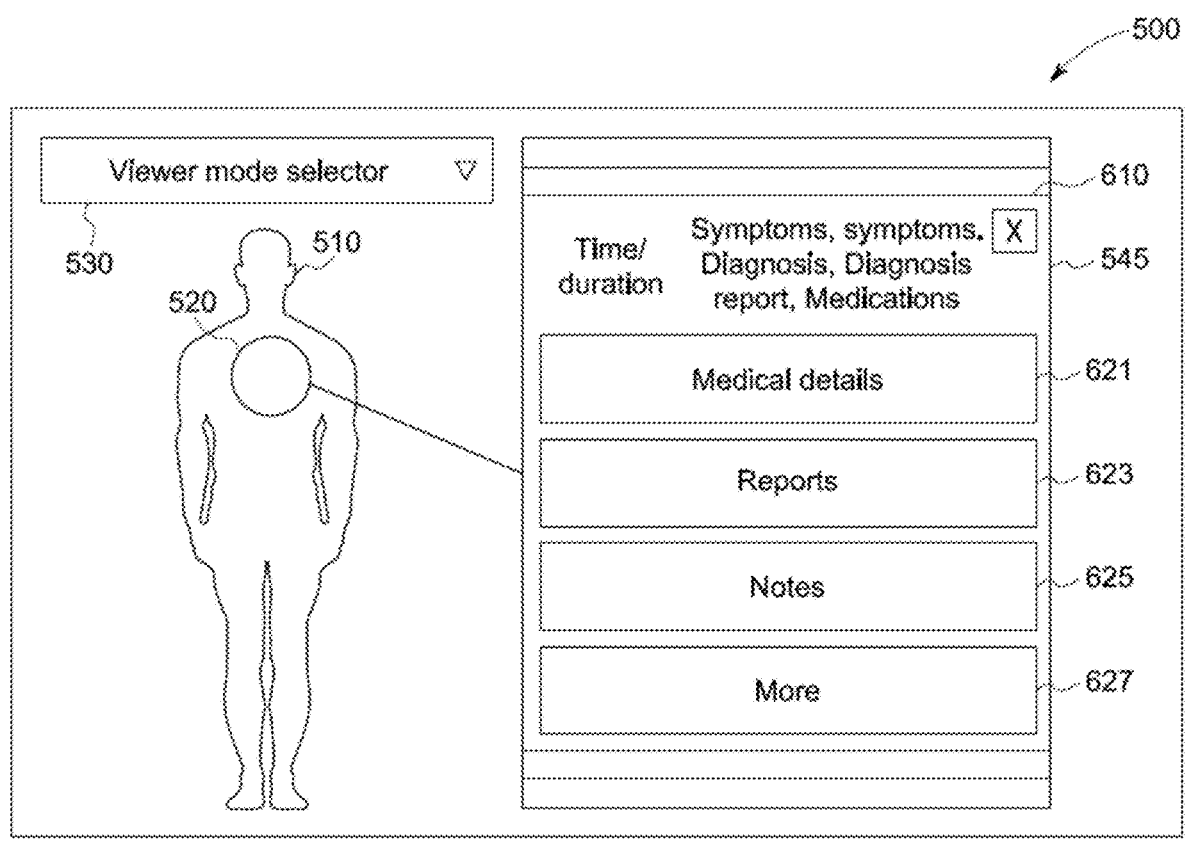

In certain examples, selecting a row, segment, or entry 541-549 of the rotor 540 reveals medical details regarding the entry 541-549. Depending on screen size and/or interface 500 configuration, the patient health detail can expand or contract to fit available space/screen real estate. FIG. 6 shows an example view of the user interface 500 providing a patient health information detail panel 610 corresponding to a selected row of the rotor 540 and indicator 520 of the visual representation 510. In this detail view of the example of FIG. 6, the detail panel 610 provides the selected/designated/default rotor 540 entry 545 expanded to show one or more medical detail, report, note, etc. 621-627. Selection of a detail 621-627, indicator 520, etc., can display further information, for example.

Figure 7:
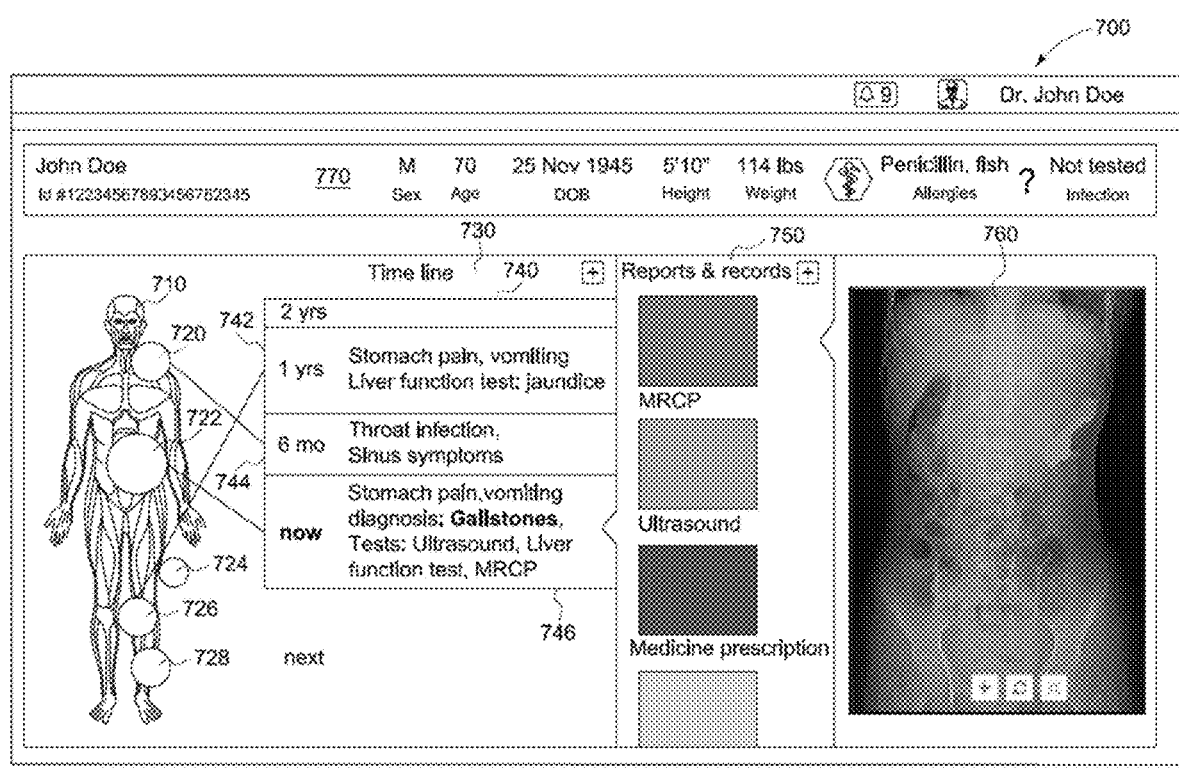

FIG. 7 illustrates an alternate implementation of a graphical user interface 700. As shown in the example of FIG. 7, the interface 700 includes a visual representation 710 of a patient's anatomy and one or more indicators 720-728 corresponding to records, images, exams, lab results, monitored data, events, etc., in the patient's health history. As in the examples of FIGS. 5 and 6, the indicators 720-728 are positioned with respect to a relevant area of the patient's anatomy corresponding to the patient's health data and appear based on manipulation of a rotor 740. One or more indicators 720-728 can be associated with each item, entry, position, etc., 742-746 in the rotor 740. A type or mode of the rotor 740 can be set by a selector 730, for example. An item or entry 742-746 in the rotor 740 can be selected to display corresponding indicator(s) 720-728 and associated source data 750, such as reports and records including images, prescriptions, exam notes, lab results, instructions, recorded sensor data, etc.

As shown in the example of FIG. 7, a thumbnail or icon indicating a source data 750 can be selected to display the data in a larger view 760. As such, an image thumbnail 750 can be selected to display the corresponding image 760 via the interface 700, for example. Annotations can be reviewed and/or added to the image 760 via the interface 700, for example.

The example graphical user interface 700 of FIG. 7 can also included a banner or header 770. The example header 770 identifies the patient, provides vitals and/or identifying information regarding the patient, etc. The header 770 can convey allergies, alerts, and/or other warnings, etc., and can convey patient and/or exam status, etc.

As such, the user interface generator 150 can generate the interface 500, 700 using patient health information, appointment/scheduling information, resource availability, healthcare protocol, external input, etc. Updates, outcomes, trends, predictions, etc., can be generated using the digital twin 140 and/or other AI model and displayed via the user interface, conveyed to another system, device, application, user, etc., via the communication interface 110, etc.

Figure 8:
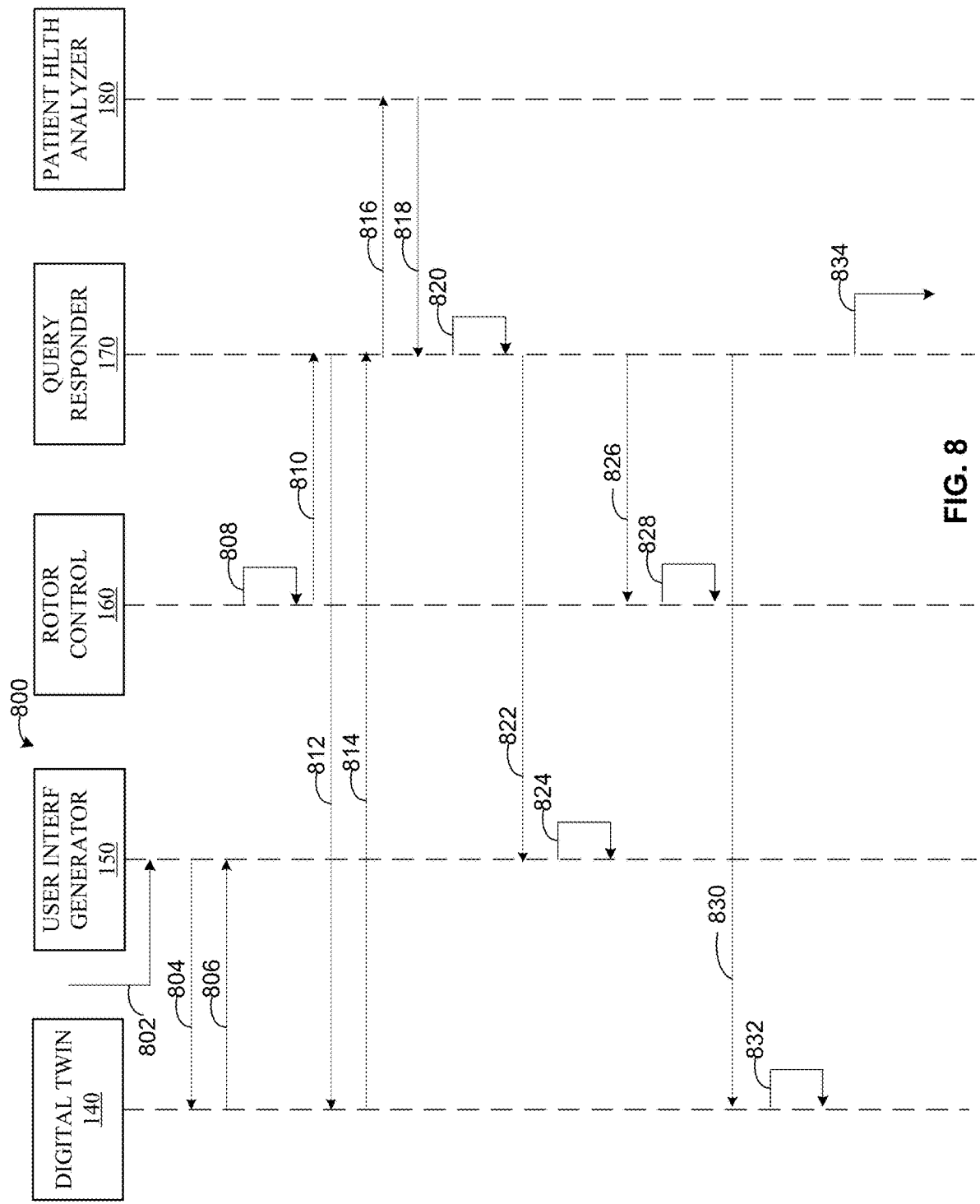
FIG. 8 depicts an example data flow among elements of the example processor of FIG. 1.

FIG. 8 depicts an example data flow 800 among elements of the example processor 130 to generate and update the digital twin 140, graphical user interface, and associated patient health diagnosis, prediction, update, etc.

At 802, the user interface generator 150 is triggered to generate and/or update a graphical user interface 500, 700. For example, the trigger can be provided from an application, system, device user, etc., via the communication interface 110 to initiate generation of the user interface. The user interface generator 150 can be triggered to generate and/or update the graphical user interface 500, 700 in response to the launching of an application on a device, for example.

At 804, the user interface generator 150 queries the digital twin 140 for patient health information to generate the graphical user interface. For example, the user interface generator 150 queries the digital twin 140 to retrieve information regarding the patient and his/her health history to form the visual representation 510, 710 and associated indicator(s) 520-528, 720-728, rotor 540, 610, 740 to display for interaction via the interface 500, 700. At 806, the digital twin 140 provides a response (e.g., patient health data, predictive outcome, data correlation, etc.) to the user interface generator 150.

At 808, the rotor control 160 receives an input via the rotor 540, 740 displayed on the interface 500, 700. For example, a segment 541-549, 742-746 of the rotor 540, 740 can be selected, a mode 530, 730 can be chosen, a data entry 621-627 can be opened via the rotor 540, 740 for example. At 810, the rotor control 160 translates the input into a query for the query responder 170. For example, selection of a segment 541-549, 742-746 and/or other entry 621-627 of the rotor 540, 740 triggers a retrieval of a corresponding time period of data, event, exam, encounter, etc.

At 812, the query responder 170 interrogates the digital twin 140 in response to the query. For example, based on the selection of a segment 541-549, 742-746, entry 621-627, etc., the query responder 170 requests corresponding information from the digital twin 140 (e.g., patient health information of a selected type, corresponding date, associated event, etc.). At 814, the digital twin 140 provides a response to the query responder 170. For example, the digital twin 140 provides patient health data, a predictive outcome, a data correlation, etc., in response to the query from the query responder 170.

At 816, the query responder 170 interrogates the patient health analyzer 180 in response to the query. For example, based on the information from the digital twin 140 and/or the query, the query responder 170 requests an analysis from the patient health analyzer 180. At 818, the patient health analyzer 180 provides a response to the query responder 170. For example, the patient health analyzer 180 provides an analysis of patient health data, predictive outcome, data correlation, etc., provided by the digital twin 140 in response to the query from the query responder 170.

At 820, the query responder 170 formulates a response to the query by processing information from the digital twin 140 and the patient health analyzer 180. For example, in response to selecting a rotor 540, 740 segment 541-549, 742-746, and/or entry 621-627, the query responder 170 formulates a query response to update the user interface display 500, 700, output information and/or other content, etc.

At 822, the query responder 170 provides the query response to the user interface generator 150. For example, the query responder 170 provides updated information for the visual representation 510, 710, associated indicator(s) 520-528, 720-728, reports/records 750, and/or source document 760, etc., to the user interface generator 150. At 824, the user interface generator 150 updates the user interface 500, 700 based on the query response. For example, one or more of the visual representation 510, 710, associated indicator(s) 520-528, 720-728, reports/records 750, and/or source document 760, etc., are updated via the displayed user interface 500, 700 for interaction, etc.

At 826, the query responder 170 provides the query response to the rotor control 160. For example, the query responder 170 provides updated information for the rotor 540, 740 segments 541-549, 742-746, and/or data entries 621-627, etc., to the rotor control 160. At 828, the rotor control 160 updates the rotor 540, 740 based on the query response. For example, one or more of the rotor 540, 740 segments 541-549, 742-746, and/or data entries 621-627, etc., are updated by the rotor control 160 for display and interaction via the displayed user interface 500, 700.

At 830, the query responder 170 provides the query response to the digital twin 140. For example, processed data forming the query response based on information from the digital twin 140 and/or patient health analyzer 180 can be fed back into the digital twin 140. At 832, the digital twin 140 updates based on the query response. For example, an AI model can be updated (e.g., trained, retrained, tested, etc.) based on information in the query response. Behavior of a system and/or sub-system of the digital twin 140 can be modified and/or otherwise updated by the query response, for example.

At 834, the query responder 170 provides the query response to the communication interface 110. For example, the query responder 170 provides the query response to be transmitted to an external system, device, application, user, etc. For example, the query responder 170 can output the query response information via the communication interface 110 to an electronic medical record system (e.g., with a patient record update, etc.), a hospital information system (e.g., to schedule an event for the patient, etc.), an imaging system (e.g., to configure the imaging device for imaging of the patient), a lab information system (e.g., to order a set of labs for the patient, etc.), a radiology information system (e.g., for patient exam reading and reporting, etc.), a picture archiving and communication system (e.g., for image processing, annotation, storage, etc.), and/or other system/device/etc.

Thus, data can be provided from a plurality of sources via the communication interface 110 and organized by the query responder 170, patient health analyzer 180, and/or digital twin 140 to model patient behavior, patient health status, patient health prediction, treatment plan/care pathway, etc. The patient health analyzer 180 and/or the digital twin 140 include one or more AI models to correlate data from disparate sources and provide an integrated, interactive interface 500, 700 with visual representation 510, 710 and indication(s) 520-528, 720-728 of patient health information, events, exams, encounters, other patient information, etc. As such, the example processor 130 can import information from a patient's electronic medical record, exam reading report, lab result, healthcare protocol, diagnosis information, treatment recommendation, etc., and provide a coordinated picture of past, present, and future patient health and facilitate further analysis, retrieval of information, and execution of health, diagnostic, and/or treatment protocol with respect to the patient via the interface 500, 700.

Using the interface 500, 700, a user can navigate to a specific file, specific treatment, specific event, etc., to access associated details. Selection can be made via anatomy on the visual representation 510, 710, indicator 520-528, 720-728, rotor 540, 740, to retrieve and view related records, selected image/file, etc. Using the rotor 540, 740, the interface 500, 700 can navigate through a patient's life, playing through the patient's record and associated details based on interaction with the interface 500, 700. As records are traversed via the rotor 540, 740, the visual representation 510, 710 and its indicators 520-528, 720-728 provide a visualization of an anatomical location and/or pattern of anatomical locations for given patient health events over time, for example. As the rotor 540, 740 is used to scroll through a list of items 541-549, 742-746, the indicators 520-528, 720-728 change in concert with the selected/visible rotor segment 541-549, 742-746. As such, the interface 500, 700 visualizes how a problem moves from one anatomical location to another and manifests different symptoms/issues, resulting in different treatment/prognosis, for example. The life cycle of the patient and his/her anatomy are visualized 510, 710 in transformation over time. Paired with the digital twin 140, all data available for the patient are mapped, correlated, analyzed, and tied to the visual 510, 710. In certain examples, a viewer mode selector 530, 730 allows data to be filtered, such as using an AI model of the digital twin 140, query responder 170, patient health analyzer 180, etc., to show a subset of available patient-related information, such as cancer-related issues, bone-related issues/diseases/symptoms, etc. Based on mode, the rotor 540, 740 surfaces that subset for navigation/manipulation, for example.

Figure 9:
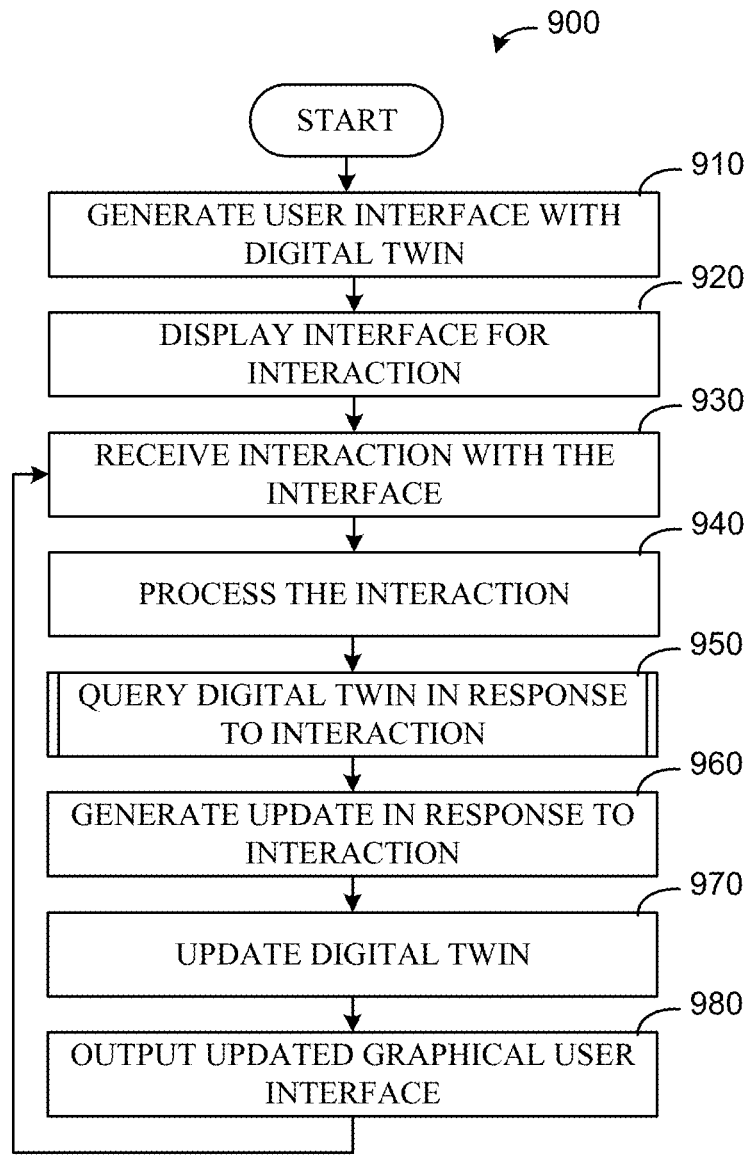
FIGS. 9-10 are flow diagrams of example methods to generate and update a graphical user interface and associated digital twin using the example apparatus of FIG. 1.

FIG. 9 is a flow diagram of an example method 900 to generate and update a graphical user interface 500, 700 and associated digital twin 140. At block 910, the user interface 500, 700 is generated with the digital twin 140. For example, the processor 130 can generate and update the digital twin 140, graphical user interface 500, 700, and associated patient health diagnosis, prediction, update, etc. For example, a trigger can be provided from an application, system, device user, etc., via the communication interface 110 to initiate generation of the user interface. The user interface generator 150 can be triggered to generate and/or update the graphical user interface 500, 700 in response to the launching of an application on a device, for example. The user interface generator 150 can query the digital twin 140, the patient health analyzer 180, etc., to retrieve information regarding the patient and his/her health history to form the visual representation 510, 710 and associated indicator(s) 520-528, 720-728, rotor 540, 610, 740 to display for interaction via the interface 500, 700.

At block 920, the graphical user interface is displayed for interaction. For example, the user interface generator 150 provides the graphical user interface 500, 700 for display and interaction via a touchscreen, display screen/monitor/television with an input device such as a keyboard, keypad, pointing device (e.g., mouse, trackpad, trackball, etc.), etc. The interface 500, 700 can be displayed for interaction on a computer monitor, smart phone, tablet computer, laptop computer, television, projector, etc.

At block 930, interaction with the graphical user interface is received. For example, the rotor control 160 can receive an input via the rotor 540, 740 displayed on the interface 500, 700. A segment 541-549, 742-746 of the rotor 540, 740 can be selected, a mode 530, 730 can be chosen, a data entry 621-627 can be opened via the rotor 540, 740, for example. Alternatively or in addition, an indicator 520-528, 720-728 displayed on the visual representation 510, 710 can be selected. The indicator 520-528, 720-728 corresponds to an anatomical location, event, exam, image, identified problem area, predicted problem area, etc., for the patient. Selection of the indicator 520-528, 720-728 triggers retrieval of further information corresponding to the indicator 520-528, 720-728 such as in reports/records 750, source document 760, etc., in the example of FIG. 7.

At block 940, the interaction is processed. For example, the rotor control 160 translates the input into a query for the query responder 170. Selection of a segment 541-549, 742-746 and/or other entry 621-627 of the rotor 540, 740 triggers a retrieval of a corresponding time period of data, event, exam, encounter, etc. Alternatively or in addition, selection of the indicator 520-528, 720-728 triggers retrieval of further information corresponding to the indicator 520-528, 720-728 such as in reports/records 750, source document 760, etc. The interaction via the rotor 540, 740, visual representation 510, 710, indicator 520-528, 720-728, etc., is processed to form a query of the digital twin 140 and/or patient health analyzer 180 to 1) provide new information for display via the interface 500, 700 (e.g., retrieve and display report/record 750, source document 760, etc.); 2) update rotor segments 541-549, 742-746, rotor items 621-627, visual representation 510, 710, and/or indicators 520-528, 720-728, etc.; 3) trigger prediction/analysis with respect to patient health; 4) communicate with an external system/device/application, etc.

At block 950, the digital twin 140 is queried in response to the interaction. For example, the query responder 170 interrogates the digital twin 140 in response to the query. For example, based on the selection of a segment 541-549, 742-746, entry 621-627, etc., the query responder 170 requests corresponding information from the digital twin 140 (e.g., patient health information of a selected type, corresponding date, associated event, etc.). The digital twin 140 can include and/or be linked to (e.g., have a pointer to, etc.) a source document from an external system, for example. The digital twin 140 can provide the source document, correlation between source document(s) and/or patient health data, analysis of source document(s) and/or patient health data, prediction of patient health diagnosis, treatment outcome, etc., based on source document(s) and/or data, etc.

In certain examples, the patient health analyzer 180 can be queried as well as the digital twin 140. For example, based on the information from the digital twin 140 and/or the query, the query responder 170 requests an analysis from the patient health analyzer 180. At 818, the patient health analyzer 180 provides a response to the query responder 170 and/or the digital twin 140. For example, the patient health analyzer 180 provides an analysis of patient health data, predictive outcome, data correlation, etc., provided by the digital twin 140 in response to the query from the query responder 170.

At block 960, an update in response to the interaction is generated. For example, the query responder 170 processes output from the digital twin 140 and/or the patient health analyzer 180 to generate an update in response to the query, which was triggered by the user interface interaction. A change in rotor segment 540-549, 742-746, entry 621-627, visual representation 510, 710, associated indicator(s) 520-528, 720-728, reports/records 750, and/or source document 760, etc., can form the update. A transmission via the communication interface 110 to an external device, system, application, etc., can form the update, for example. The update can provide new content, changed content, computer-aided diagnosis, diagnosis and/or treatment prediction, etc., based on the digital twin 140 model(s) and/or patient health analyzer 180 analysis of model output and/or other patient health data, rule(s), criterion(-ia), etc.

At block 970, the digital twin 140 is updated. For example, processed data forming a response to the query triggered by the user interface interaction, generated based on information from the digital twin 140 and/or patient health analyzer 180, can be fed back into the digital twin 140. For example, an AI model can be updated (e.g., trained, retrained, tested, etc.) based on information in the query response. Behavior of a system and/or sub-system of the digital twin 140 can be modified and/or otherwise updated by the query response, for example.

At block 980, an updated graphical user interface 500, 700 is output. For example, the query responder 170 formulates an update to the user interface 500, 700 in response to the interaction/query by processing information from the digital twin 140 and the patient health analyzer 180. For example, in response to selecting a rotor 540, 740 segment 541-549, 742-746, and/or entry 621-627, the query responder 170 formulates a query response to update the user interface display 500, 700, output information and/or other content, etc. The query responder 170 provides updated information for the visual representation 510, 710, associated indicator(s) 520-528, 720-728, reports/records 750, and/or source document 760, etc., to the user interface generator 150. The user interface generator 150 updates the user interface 500, 700 based on the query response. For example, one or more of the visual representation 510, 710, associated indicator(s) 520-528, 720-728, reports/records 750, and/or source document 760, etc., are updated via the displayed user interface 500, 700 for interaction, etc. The update can impact the rotor control 160 to update rotor segments 541-549, 742-746 and/or data entries 621-627, for example.

In certain examples, the query responder 170 provides an update and/or other output via the communication interface 110 to an external system, device, application, user, etc. For example, the query responder 170 can output the query response information via the communication interface 110 to an electronic medical record system (e.g., with a patient record update, etc.), a hospital information system (e.g., to schedule an event for the patient, etc.), an imaging system (e.g., to configure the imaging device for imaging of the patient), a lab information system (e.g., to order a set of labs for the patient, etc.), a radiology information system (e.g., for patient exam reading and reporting, etc.), a picture archiving and communication system (e.g., for image processing, annotation, storage, etc.), and/or other system/device/etc.

Thus, a graphical user interface 500, 700 and associated model(s) 140 of a patient and/or patient health data can be generated and interrelated for interaction and update to drive new systems and methods for patient data display, simulation, correlation, and workflow guidance. Certain examples drive patient diagnosis and treatment through the graphical user interface 500, 700 and associated digital twin 140. One or more AI models, such as convolutional neural network (CNN), deep neural network (DNN), random forest (RF), reinforcement learning (RL), long short-term memory model, recurrent neural network (RNN), etc., can model patient health data, condition(s), treatment(s), care plan(s), etc., to drive both user interface display and action regarding patient diagnosis, treatment, and follow-up. For example, the digital twin 140 and associated AI model(s) provide a technological improvement in electronic medical record systems and associated displays to model patient health data, drive action with respect to other health systems (e.g., HIS, RIS, CIS, CVIS, PACS, LIS, EMR, etc.). The patient health analyzer 180 and/or the digital twin 140 include one or more AI models to correlate data from disparate sources and provide an integrated, interactive interface 500, 700 with visual representation 510, 710 and indication(s) 520-528, 720-728 of patient health information, events, exams, encounters, other patient information, etc. As such, the example processor 130 can import information from a patient's electronic medical record, exam reading report, lab result, healthcare protocol, diagnosis information, treatment recommendation, etc., and provide a coordinated picture of past, present, and future patient health and facilitate further analysis, retrieval of information, and execution of health, diagnostic, and/or treatment protocol with respect to the patient via the interface 500, 700.

Figure 10:
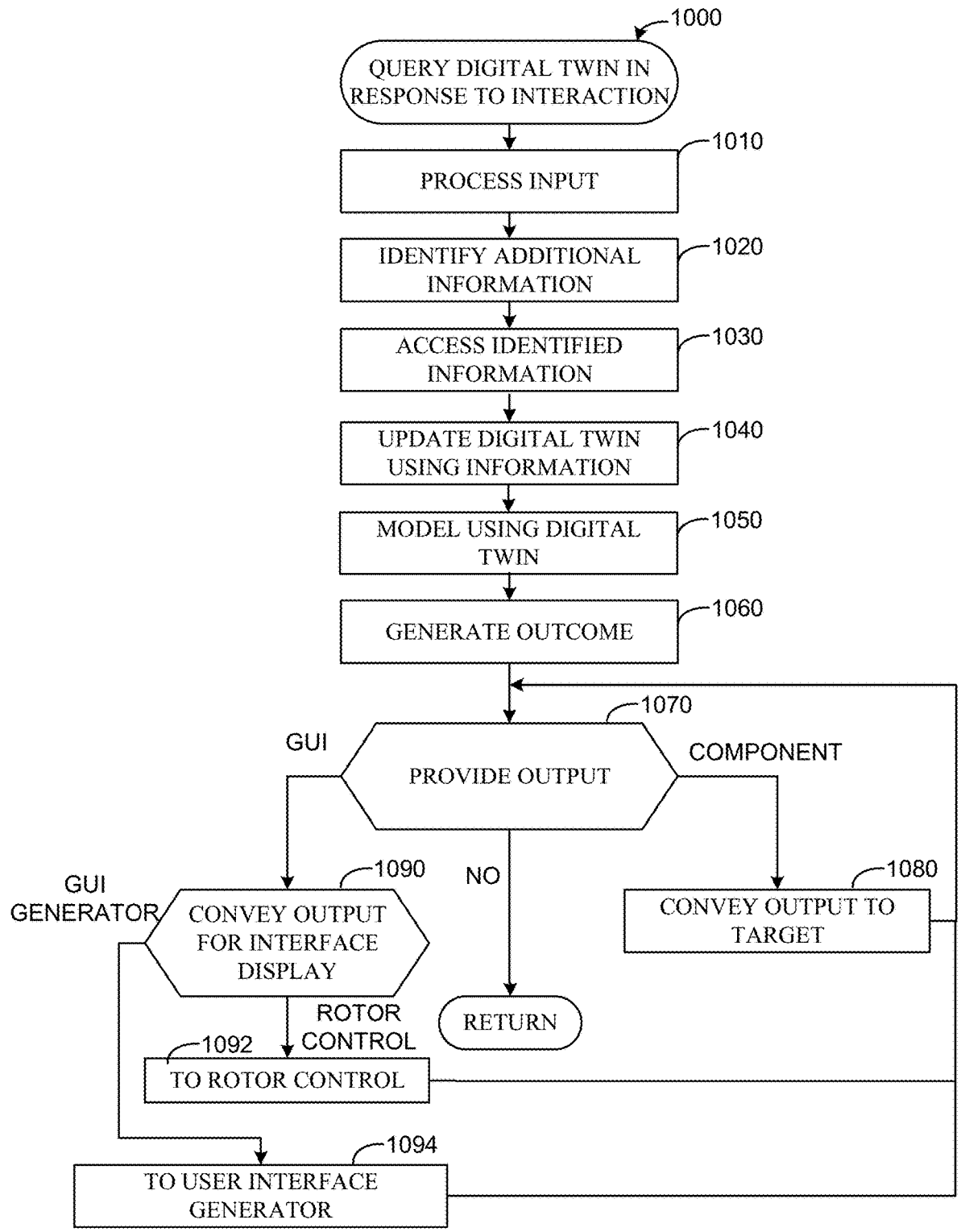

FIG. 10 is a flow diagram of an example method 1000 to query the digital twin 140 in response to interaction with the graphical user interface 500, 700 (e.g., block 950 of the example of FIG. 9). As such, the digital twin 140 can process user interface 500, 700 interaction to drive an update to the user interface 500, 700 as well as trigger action(s) for other system(s), application(s), device(s), etc., to execute functions (e.g., order lab test, schedule an appointment, obtain an image, analyze an image, generate instructions for treatment, develop a care plan, interconnect systems/applications/devices and associated data, etc.). At block 1010, an input is processed. For example, the input is processed to understand the input and understand how the input relates to the model(s) included in the digital twin 140. The input can be interpreted by the digital twin 140 as a question, query, update, current interface state, updated patient data, updated protocol, updated device information, sensor data, image, etc. Such input triggers a next action by the digital twin 140.

At block 1020, external information needed and/or otherwise associated with a response to the input is identified. For example, patient records, image data, scheduling/availability information, etc., located eternal to the digital twin 140 can be identified. As such, some information can be modeled within the digital twin 140 and other information can be retrievable from another element of the apparatus 100 and/or an external source such as an EMR, PACS, RIS, CVIS, HIS, LIS, etc. At block 1030, the identified additional information is retrieved and/or otherwise accessed by the digital twin 140. For example, the query responder 170 can retrieve and provide the information to the digital twin 140, the digital twin 140 can retrieve and/or otherwise access the information, the information can be retrieved and/or remotely accessed via the communication interface 110, etc.

At block 1040, the digital twin 140 is updated based on the additional information. For example, an AI model representing a patient anatomy/system, such as the patient's chest, head, limb, torso, vascular system, skeletal system, musculoskeletal system, nervous system, etc., can be trained, tested, and/or otherwise updated using the additional information to which the digital twin 140 has access (e.g., by data transfer, remote connection, etc.).

At block 1050, the digital twin 140 models one or more patient body systems, health effects, conditions, treatment, etc., based on the input. For example, in response to a query regarding cancer prediction, the digital twin 140 models the patient's skeletal system, history of fractures, etc. In response to a request to retrieve and display the patient's history of epileptic seizures, the digital twin 140 models the patient's nervous system correlated with electroencephalogram (EEG) waveform data, for example. In response to a query regarding the patient's history of diabetic blood sugar control, the digital twin 140 models the patient's endocrine system in conjunction with indications of high (e.g., hyperglycemia) and/or low (e.g., hypoglycemia) blood sugar level, A1c, etc., for example. As such, a variety of queries can be answered, outcomes predicted, health information correlated, etc., using the digital twin 140.

At block 1060, an outcome is generated by the digital twin 140. For example, the digital twin 140 can correlate patient health information, condition, symptom, factor, guideline, protocol, etc. The digital twin 140 can predict a diagnosis, outcome, correlation, treatment, etc. For example, the digital twin 140 generates a prediction of bone cancer based on the modeled skeletal system information including a history of fractures, etc., for the patient. The digital twin 140 generates a scheduled allocation of resources based on modeling of patient and hospital information, for example. The digital twin 140 generates a subset of indicators 520-528, 720-728 based on patient body system(s), date(s), condition(s), etc., modeled by the digital twin 140, for example. The digital twin 140 generates rotor 540, 740 segments 541-549, 742-746 based on modeled system, date, condition, etc.

At block 1070, output is provided by the digital twin 140 based on the outcome. For example, output can be provided to update the graphical user interface 500, 700. Alternatively or in addition, output can be provided to a component of the system 100 and/or an external system/device from the digital twin 140, for example. Output can include a visual update, a prediction, a diagnosis, a selection of treatment, a correlation of data, etc.

At block 1080, when the output includes an output for an element of the system 100 (e.g., memory 120, user interface generator 150, rotor control 160, query responder 170, patient health analyzer 180, etc.) and/or an external system/device/application, etc., the digital twin 140 provides the output to the target (e.g., directly or via the query responder 170, etc.). For example, a correlation, diagnosis, treatment recommendation, set of indicators, etc., can be stored in memory 120 and/or provided to an external system/device/application/etc. via the communication interface 110. Output can be provided internally to the processor 130 such as to the user interface generator 150, rotor control 160, query responder 170, patient health analyzer 180, etc.

At block 1090, when the output includes an output for the graphical user interface 500, 700, the digital twin 140 provides the output to the user interface generator 150 and/or the rotor control 160 to generate/update all or part of the graphical user interface display 500, 700. At block 1092, when the output applies to the display and function of the rotor 540, 740, and its segments 541-549, 742-746, the digital twin 140 provides the output to the rotor control 160 to allow the rotor control 160 to update the segments 541-549, 742-746, items 621-627, etc., on the rotor 540, 740 according to the output from the digital twin 140. At block 1094, when the output applies to the display and function of the visual representation 510, 710, indicators 520-528, 720-728, reports/records 750, document view 760, and/or other element of the graphical user interface 500, 700, the digital twin 140 provides the output to the user interface generator 150 to enable the user interface generator 150 to update content and/or functionality on the interface 500, 700. The process repeats at block 1070 until all output from the digital twin 140 has been routed appropriately. Control then returns to block 960, for example, to generate an update in response.

Thus, modeling a patient using the digital twin 140 and/or AI model(s) can be used to drive new and technologically different user interface behavior and interaction. Manipulation of an interface object, entry of a query, selection of an item, etc., triggers the digital twin/model(s) 140 to update displayed information, make correlations, generate a diagnosis, suggest a treatment, predict an outcome, track progress, coordinate a care plan with other device(s), etc. Such dynamic modeling creates a new, interactive graphical user interface to drive patient health analysis, diagnosis, treatment, and coordination among multiple resources, a patient population, a healthcare facility, a disease/condition cohort, etc. Leveraging the digital twin 140 and/or other AI model(s) to drive the graphical user interface 500, 700 improves performance of the processor 130 in facilitating system, application, and/or user interaction with the graphical user interface 500, 700 and associated system(s). The processor 130 with digital twin 140, user interface generator 150, rotor control 160, query responder 170, and patient health analyzer 180 represents a technological improvement in user interface generation, model-driven updates, and interaction between systems, applications, and users via the digital twin 140, visual representation 510, 710, indicators 520-528, 720-728, rotor 540, 740, etc.

Certain examples improve patient record management, patient health modeling, and interactive interfacing by modeling and providing a "live" patient record which enables visualization of the patient's life and details including health events, exams, conditions, images, etc. Through the digital twin 140 and interface 500, 700, affected area(s) of the patient can be traversed over both location and time. The rotor 540, 740 enables traversal and filtering based on time, location, condition, body system, anatomy, healthcare provider, and/or other criterion, for example. Rather than a subset, all of the patient's health data can be made available and can be filtered and/or otherwise divided into subsets based on mode, rotor interaction, indicator selection, etc. Non-health events can be correlated with health events using AI model(s) and conveyed for interaction via the graphical user interface, for example.

In certain examples, as the rotor 540, 740 is used to scroll through the patient's health data, the indicators 520-528, 720-728 on the visual representation 510, 710 of the patient anatomy change to illustrate different issues, how a problem moves from one place to another, and/or otherwise demonstrate a pattern in that patient's health. The interface 500, 700 and associated digital twin 140 allow modeling, visualization, and interaction with an entire life cycle of a human body as the patient is transforming over time. The digital twin 140 maps the patient's data, other environment and/or best practice data, etc., and uses the data to drive the visual. In certain examples, a mode 530, 730 can be selected to enable the AI to filter on one or more criterion (e.g., all, by disease type, by body part, by date, by location, by provider, by protocol, by other condition, etc.). The rotor 540, 740 then only shows that subset of data for traversal, selection, and/or other interaction.

While example implementations are disclosed and described herein, processes and/or devices disclosed and described herein can be combined, divided, re-arranged, omitted, eliminated and/or implemented in any other way. Further, components disclosed and described herein can be implemented by hardware, machine readable instructions, software, firmware and/or any combination of hardware, machine readable instructions, software and/or firmware. Thus, for example, components disclosed and described herein can be implemented by analog and/or digital circuit(s), logic circuit(s), programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the components is/are hereby expressly defined to include a tangible computer readable storage device or storage disk such as a memory, a digital versatile disk (DVD), a compact disk (CD), a Blu-ray disk, etc. storing the software and/or firmware.

Flowcharts representative of example machine readable instructions for implementing components are disclosed and described herein. In the examples, the machine readable instructions include a program for execution by a processor. The program may be embodied in machine readable instructions stored on a tangible computer readable storage medium such as a CD-ROM, a floppy disk, a hard drive, a digital versatile disk (DVD), a Blu-ray disk, or a memory associated with the processor, but the entire program and/or parts thereof could alternatively be executed by a device other than the processor and/or embodied in firmware or dedicated hardware. Further, although the example program is described with reference to flowchart(s), many other methods of implementing the components disclosed and described herein may alternatively be used. For example, the order of execution of the blocks may be changed, and/or some of the blocks described may be changed, eliminated, or combined. Although the flowchart(s) depict example operations in an illustrated order, these operations are not exhaustive and are not limited to the illustrated order. In addition, various changes and modifications may be made by one skilled in the art within the spirit and scope of the disclosure. For example, blocks illustrated in the flowchart may be performed in an alternative order or may be performed in parallel.

As mentioned above, the example process(es) can be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example process(es) can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. In addition, the term "including" is open-ended in the same manner as the term "comprising" is open-ended.

Figure 11:
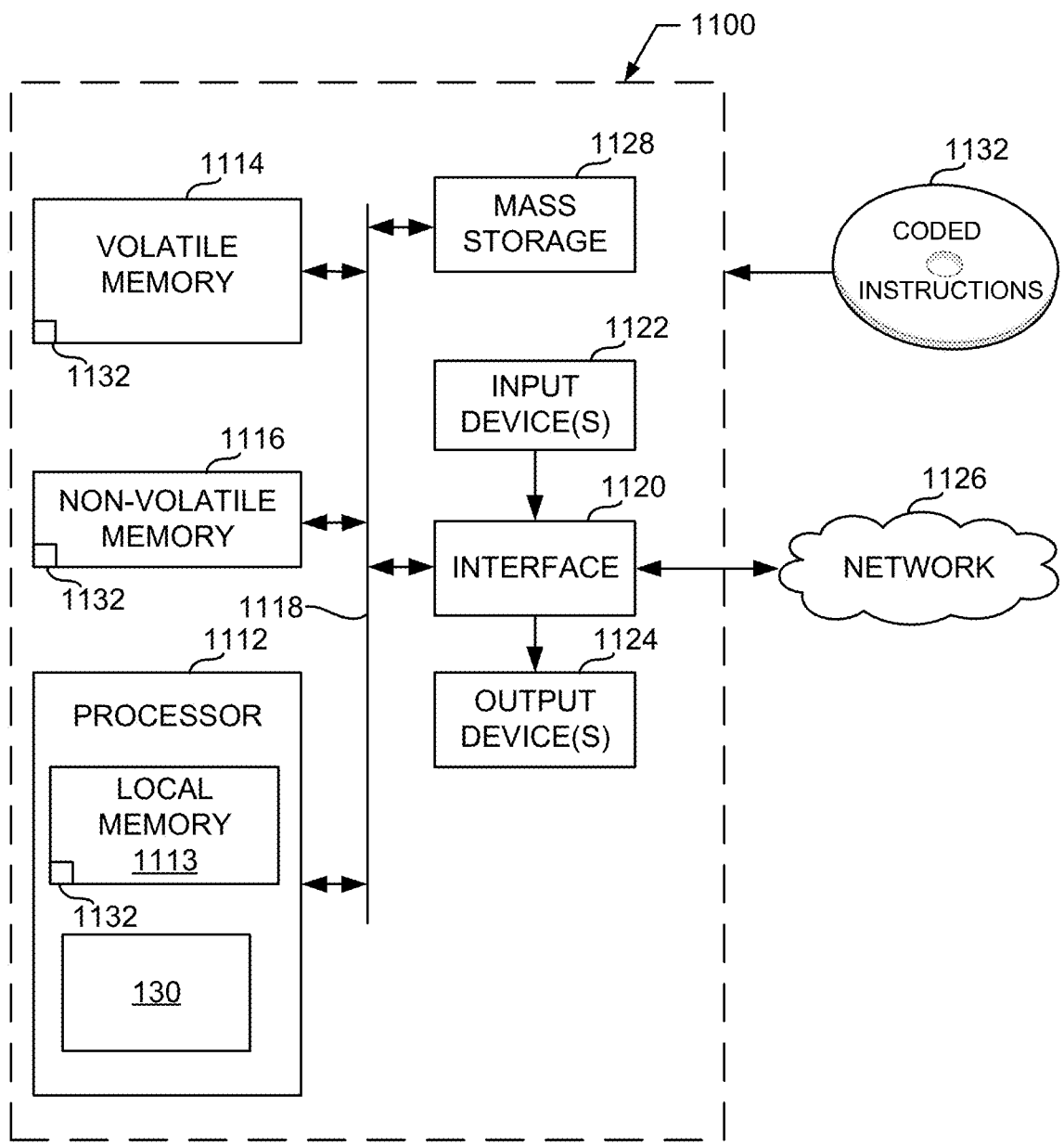
FIG. 11 is a block diagram of an example processor platform capable of executing instructions to implement the example systems and methods disclosed and described herein.

FIG. 11 is a block diagram of an example processor platform 1100 structured to execute the instructions of FIGS. 8-10 to implement, for example the example apparatus 100 and other systems, apparatus, etc., of FIGS. 1-7. The processor platform 110 can be, for example, a server, a personal computer, a workstation, a self-learning machine (e.g., a neural network), a mobile device (e.g., a cell phone, a smart phone, a tablet such as an iPad'), a personal digital assistant (PDA), an Internet appliance, a gaming console, a personal video recorder, a set top box, a headset or other wearable device, or any other type of computing device.

The processor platform 1100 of the illustrated example includes a processor 1112. The processor 1112 of the illustrated example is hardware. For example, the processor 1112 can be implemented by one or more integrated circuits, logic circuits, microprocessors, GPUs, DSPs, or controllers from any desired family or manufacturer. The hardware processor may be a semiconductor based (e.g., silicon based) device. In this example, the processor 1112 implements the example processor 130 apparatus 100 but can also be used to implement other systems disclosed herein.

The processor 1112 of the illustrated example includes a local memory 1113 (e.g., a cache). The processor 1112 of the illustrated example is in communication with a main memory including a volatile memory 1114 and a non-volatile memory 1116 via a bus 1118. The volatile memory 1114 may be implemented by SDRAM, DRAM, RDRAM®, and/or any other type of random access memory device. The non-volatile memory 1116 may be implemented by flash memory and/or any other desired type of memory device. Access to the main memory 1114, 1116 is controlled by a memory controller. The example memory 120 can be implemented using the local memory 113, volatile memory 1114, and/or non-volatile memory 1116, for example.

The processor platform 1100 of the illustrated example also includes an interface circuit 1120. The interface circuit 1120 may be implemented by any type of interface standard, such as an Ethernet interface, a USB, a Bluetooth® interface, an NFC interface, and/or a PCI express interface. The example communication interface 110 can be implemented using the interface circuit 1120, for example.

In the illustrated example, one or more input devices 1122 are connected to the interface circuit 1120. The input device(s) 1122 permit(s) a user to enter data and/or commands into the processor 1112. The input device(s) can be implemented by, for example, an audio sensor, a microphone, a camera (still or video), a keyboard, a button, a mouse, a touchscreen, a track-pad, a trackball, isopoint, and/or a voice recognition system.

One or more output devices 1124 are also connected to the interface circuit 1120 of the illustrated example. The output devices 1124 can be implemented, for example, by display devices (e.g., an LED, an OLED, an LCD, a CRT display, an IPS display, a touchscreen, etc.), a tactile output device, a printer, and/or speaker. The interface circuit 1120 of the illustrated example, thus, typically includes a graphics driver card, a graphics driver chip, and/or a graphics driver processor.

The interface circuit 1120 of the illustrated example also includes a communication device such as a transmitter, a receiver, a transceiver, a modem, a residential gateway, a wireless access point, and/or a network interface to facilitate exchange of data with external machines (e.g., computing devices of any kind) via a network 1126. The communication can be via, for example, an Ethernet connection, a DSL connection, a telephone line connection, a coaxial cable system, a satellite system, a line-of-site wireless system, a cellular telephone system, etc.

The processor platform 1100 of the illustrated example also includes one or more mass storage devices 1128 for storing software and/or data. Examples of such mass storage devices 1128 include floppy disk drives, hard drive disks, compact disk drives, Blu-ray disk drives, RAID systems, and DVD drives.

The machine executable instructions 1132 of FIGS. 9-10 may be stored in the mass storage device 1128, in the volatile memory 1114, in the non-volatile memory 1116, and/or on a removable non-transitory computer readable storage medium such as a CD or DVD.

From the foregoing, it will be appreciated that example methods, apparatus and articles of manufacture have been disclosed that generate and drive interaction with new, technologically improved interfaces and digital twin/AI models. As such, certain examples improve the capabilities, efficiency, and effectiveness of processor system, memory, and other associated circuitry by leveraging artificial intelligence models, transformations and expansions of patient health data, comparative analysis of patient data, etc. The disclosed methods, apparatus and articles of manufacture are accordingly directed to one or more improvement(s) in the functioning of a computer and/or other processor and its associated interface. The apparatus, methods, systems, instructions, and media disclosed herein are not implementable in a human mind and are not able to be manually implemented by a human user.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. An apparatus comprising:
  memory including instructions; and
  at least one processor to execute the instructions to generate at least:
    a digital twin of a patient, the digital twin to include models of a patient based on patient health data, the models representing the patient in a virtual space and enabling analysis of the patient within the virtual space, the digital twin including a link between the patient health data and the virtual space; and a graphical user interface to provide visualization of and access to the patient health data based on an output from the digital twin, the graphical user interface to include:

a visual representation of patient anatomical systems, the visual representation to include selectable indicators corresponding to the patient health data; and a rotor paired with the digital twin, the rotor including categories of the patient health data, the rotor selectable via the graphical user interface (i) to navigate a subset of the patient health data corresponding to a selected category via the visual representation of the patient and (ii) to trigger at least one of an activation or a configuration of at least one of the models to generate, using at least one of the models and the subset of patient health data, at least one of:

a visual simulation of a patient's physical behaviors;

an analysis of patient health data driven by rotor selection; or a prediction of a patient health outcome.

2. The apparatus of claim 1, wherein the models of patient health data are implemented using one or more artificial intelligence models.

3. The apparatus of claim 1, wherein the categories include one or more of location, time, condition, or anatomy type.

4. The apparatus of claim 1, wherein the rotor is to display segments, each segment corresponding to a category of the patient health data, and wherein selection of a segment triggers highlighting and navigating of one or more indicators on the visual representation.

5. The apparatus of claim 4, wherein the graphical user interface further includes a mode selector, the mode selector to apply a filter to the segments and associated categories of the rotor.

6. The apparatus of claim 1, wherein the digital twin is to generate the output, when triggered by interaction with the graphical user interface, from at least one of the models of patient health data or the models of patient anatomical systems with respect to a criterion corresponding to at least one of an indicator or the rotor of the graphical user interface.

7. The apparatus of claim 6, wherein the digital twin is to update based on at least one of the interaction with the graphical user interface or the output.

8. The apparatus of claim 6, wherein the output includes a prediction of at least one of diagnosis or treatment of a condition, the output to be visible via the graphical user interface and to trigger a follow-up action when selected via the graphical user interface.

9. The apparatus of claim 4, wherein the mode selector is to adjust selection available via the rotor based on the selected mode and to drive output from at least one of the models based on the selected mode.

10. The apparatus of claim 1, wherein the digital twin is to age in the virtual space along with the patient in a real space, the aging of the patient based on at least one of the models and the patient health data.

11. At least one tangible computer-readable storage medium comprising instructions that, when executed, cause at least one processor to at least:

a digital twin of a patient, the digital twin to include models of a patient based on patient health data, the models representing the patient in a virtual space and enabling analysis of the patient within the virtual space, the digital twin including a link between the patient health data and the virtual space; and a graphical user interface to provide visualization of and access to the patient health data based on an output from the digital twin, the graphical user interface to include:

a visual representation of patient anatomical systems, the visual representation to include selectable indicators corresponding to the patient health data; and a rotor paired with the digital twin, the rotor including categories of the patient health data, the rotor selectable via the graphical user interface (i) to navigate a subset of the patient health data corresponding to a selected category via the visual representation of the patient and (ii) to trigger at least one of an activation or a configuration of at least one of the models to generate, using at least one of the models and the subset of patient health data, at least one of:

a visual simulation of a patient's physical behaviors;

an analysis of patient health data driven by rotor selection; or a prediction of a patient health outcome.

12. The at least one tangible computer-readable storage medium of claim 11, wherein the models of patient health data are implemented using one or more artificial intelligence models.

13. The at least one tangible computer-readable storage medium of claim 11, wherein the categories include one or more of location, time, condition, or anatomy type.

14. The at least one tangible computer-readable storage medium of claim 11, wherein the instructions, when executed, cause the rotor to display segments, each segment corresponding to a category of the patient health data, and wherein selection of a segment triggers highlighting and navigating of one or more indicators on the visual representation.

15. The at least one tangible computer-readable storage medium of claim 14, wherein the graphical user interface further includes a mode selector, the mode selector to apply a filter to the segments and associated categories of the rotor.

16. The at least one tangible computer-readable storage medium of claim 11, wherein the instructions, when executed, cause the digital twin to generate the output, when triggered by interaction with the graphical user interface, from at least one of the models of patient health data or the models of patient anatomical systems with respect to a criterion corresponding to at least one of an indicator or the rotor of the graphical user interface.

17. The at least one tangible computer-readable storage medium of claim 16, wherein the instructions, when executed, cause the digital twin to update based on at least one of the interaction with the graphical user interface or the output.

18. The at least one tangible computer-readable storage medium of claim 16, wherein the output includes a prediction of at least one of diagnosis or treatment of a condition, the output to be visible via the graphical user interface and to trigger a follow-up action when selected via the graphical user interface.

19. A computer-implemented method to generate an interactive graphical user interface, the method comprising:

generating, using a digital twin of a patient, a graphical user interface including a visual representation of patient anatomy and a rotor paired with the digital twin, the rotor including categories of patient health data, the digital twin to include models of a patient based on i) patient health data and ii) patient anatomical systems, the models representing the patient in a virtual space and enabling analysis of the patient within the virtual space, the digital twin including a link between the patient health data and the virtual space, the visual representation to include selectable indicators corresponding to at least one of the patient health data or the patient anatomical systems, and the rotor selectable via the graphical user interface to navigate a subset of the patient health data corresponding to a selected category via the visual representation of the patient;

modeling, using the digital twin when triggered by interaction with the graphical user interface, an output from at least one of the models of patient health data or the models of patient anatomical systems with respect to a criterion corresponding to at least one of an indicator or the rotor of the graphical user interface, the modeled output to include at least one of: a visual simulation of a patient's physical behaviors, an analysis of patient health data driven by the rotor selector, a prediction of a patient health outcome; and updating at least one of the digital twin or the graphical user interface using the output.

20. The method of claim 19, wherein the output includes a prediction of at least one of diagnosis or treatment of a condition, and further including updating the graphical user interface to visualize the output and triggering a follow-up action when the visualization of the output is selected via the graphical user interface.

* * * * *